US007019144B2

(12) United States Patent
Cho et al.

(10) Patent No.: US 7,019,144 B2
(45) Date of Patent: Mar. 28, 2006

(54) 1,2,4-TRIAZOLE DERIVATIVE, METHOD FOR PREPARING THE SAME, AND PHARMACEUTICAL COMPOSITION CONTAINING THE SAME

(75) Inventors: Il Hwan Cho, Seoul (KR); Hyun Jung Park, Jeonrabuk-do (KR); Ji Young Noh, Busan (KR); Hyung Chul Ryu, Yongin (KR); Sang Wook Park, Suwon (KR); Sung Hak Jung, Seoul (KR); Sung Hak Lee, Yongin (KR); Jong Hoon Kim, Anyang (KR); Jee Woong Lim, Gunpo (KR); Chun Seon Lyu, Yongin (KR); Dal Hyun Kim, Suwon (KR); Young Hoon Kim, Seoul (KR); Kyu Jeong Yeon, Yongin (KR); Myeong Yun Chae, Seongnam (KR); In Ki Min, Yongin (KR); Hae Tak Jin, Yongin (KR); Kyoung Rae Kang, Seoul (KR)

(73) Assignee: CJ Corp., (KR)

( * ) Notice: Subject to any disclaimer, the term of this patent is extended or adjusted under 35 U.S.C. 154(b) by 0 days.

(21) Appl. No.: 10/608,709

(22) Filed: Jun. 27, 2003

(65) Prior Publication Data
US 2005/0075507 A1    Apr. 7, 2005

(30) Foreign Application Priority Data
Aug. 7, 2002 (KR) .................. 10-2002-0046551

(51) Int. Cl.
    C07D 401/04    (2006.01)
    C07D 249/10    (2006.01)
    C07D 249/12    (2006.01)
    C07D 249/14    (2006.01)
(52) U.S. Cl. .................. 546/272.4; 548/267.2; 548/267.4; 548/267.8; 548/238.6; 548/269.4
(58) Field of Classification Search ............. 546/272.4; 548/267.2, 267.4, 267.8, 268.6, 269.4
See application file for complete search history.

(56) References Cited

U.S. PATENT DOCUMENTS

| 4,204,870 | A | 5/1980 | Chapman et al. | ............ 430/213 |
| 5,444,148 | A | 8/1995 | Alewelt et al. | ............ 528/196 |
| 5,466,823 | A | 11/1995 | Talley et al. | ............ 548/377.1 |
| 5,633,272 | A | 5/1997 | Talley et al. | ................. 514/378 |
| 2003/0012368 | A1 * | 1/2003 | Sakya et al. | |

FOREIGN PATENT DOCUMENTS

| EP | 1099695 | * | 5/2001 |
| EP | 1 104 759 A1 | | 6/2001 |
| WO | 95/00501 | | 1/1995 |

OTHER PUBLICATIONS

"Current Perspective Recent advances in the management of colorectal cancer"; Authors: E. Van Cutsem, M. Dicato, J. Wils; European Journal of Cancer 37; Elsevier Science Ltd.; 2001; pp. 2302-2309.
Monthly Focus: Central & Peripheral Nervous Systems; "Anti-Inflammatory drugs: a hope for Alzheimer's disease?"; Authors: Michael Hull, Klaus Lieb & Bernd L. Flebich; Asley Publications Ltd.; 2000; pp. 671-683.
News and Views; "Towards a better aspirin"; Author: John Vane; Nature, vol. 367; Jan. 20, 1994; pp. 215-216.
Meeting Report; "COX-1 and COX-2: Toward the Development of More Selective NSAIDs"; Authors: Bruno Battistini, Regina Botting and Y.S. Bakhle; DN & P 7 (8); Oct. 1994; pp. 501-512.
Chapter 19; "Selective Cycloozygenase Inhibitors"; Authors: David B. Reitz and Karen Seibert; Annual Reports in Medicinal Chemistry-30; Academic Press, Inc.; 1995; pp. 179-188.
Pergamon; "Synthesis and Biological Evaluation of 2, 3-Diarylthiophenes as Selective COX-2 and COX-1 Inhibitors"; Authors: Yves Leblanc, Jacques Yves Gauthier, Diane Ethier, Jocelyne Guay, Joseph Mancini, Denis Rlendeau, Philip Tagari, Philip Vichers, Elizabeth Wong and Petpiboon Prasit; Bioorganic & Medicinal Chemistry Letters, vol. 5, No. 18; Elsevier Science Ltd.; 1995; pp. 2123-2128.
"Synthesis and Biological Evaluation of the 1, 5-Diarylpyrazole Class of Cycloozygenase-2 Inhibitors: Identification of 4-[5-(4-Methylphenyl)-3-(trifluoromethyl)-1H-pyrazol-1-yl] benzenesulfonamide (SC-58635, Celecoxib)"; Authors: Thomas D. Penning, et al.; Journal of Medicinal Chemistry vol. 40, No. 9; American Chemical Society; 1997; pp. 1347-1365.

* cited by examiner

Primary Examiner—Patricia L. Morris
(74) Attorney, Agent, or Firm—Cantor Colburn LLP

(57) ABSTRACT

A 1,2,4-Triazole derivative of formula 1 or a non-toxic salt thereof, a preparation method thereof, and a pharmaceutical composition containing the derivative or the salt as an active ingredient are provided.

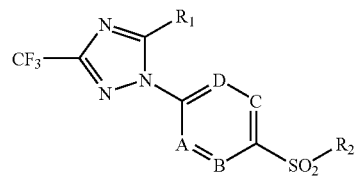

Formula 1

2 Claims, No Drawings

1,2,4-TRIAZOLE DERIVATIVE, METHOD FOR PREPARING THE SAME, AND PHARMACEUTICAL COMPOSITION CONTAINING THE SAME

BACKGROUND OF THE INVENTION

This U.S. non-provisional application claims priority under 35 U.S.C. §119 to Korean Patent Application No. 2002-46551, filed on Aug. 7, 2002, in the Korean Intellectual Property Office, the contents of which are incorporated herein by reference in its entirety.

1. Field of the Invention

The present invention relates to a 1,2,4-triazole derivative or non-toxic salt thereof, a method for preparing the same, and a pharmaceutical composition containing the same as an active ingredient.

2. Description of the Related Art

Most nonsteroidal antiinflammatory agents are responsible for blocking the enzyme, cyclooxygenase (COX) or prostaglandin G/H synthase, thereby reducing inflammation, pain, or fever. In addition, they inhibit uterus contraction caused by hormones and also inhibit growth of several cancers. Cyclooxygenase-1 (COX-1) was first discovered in bovine. The COX-1 is constitutively expressed in a variety of cell types. Unlike the COX-1, cyclooxygenase-2 (COX-2) is a recently discovered isoform of cyclooxygenase that is easily inducible by mitogen, endotoxin, hormone, growth factor, or cytokine.

Prostaglandin is a potent mediator of various pathological and physiological processes. The COX-1 plays important physiological roles such as the release of endogenous prostaglandin, the maintenance of the shape, the function of stomach, and blood circulation in kidney. On the other hand, the COX-2 is induced by an inflammatory factor, hormone, growth factor, or cytokine. Therefore, the COX-2 is involved in pathological processes of prostaglandin unlike the constitutive COX-1.

In this regard, selective inhibitors of the COX-2 produce fewer and less side effects in terms of action mechanism in comparison with conventional nonsteroidal antiinflammatory agents. In addition, they reduce inflammation, pain, and fever and inhibit uterus contraction caused by hormones and growth of several cancers. In particular, they are effective in decreasing side effects such as stomach toxicity and kidney toxicity. Still furthermore, they inhibit the synthesis of contractile prostanoid, thereby leading to suppression of the contraction of smooth muscles. Therefore, premature birth, menstrual irregularity, asthma, and eosinophilic disease can be prevented.

Recently, it was reported that nonsteroidal antiinflammatory agents are effective in treating large intestine cancer [*European Journal of Cancer*, Vol 37, p 2302, 2001], prostate cancer [*Urology*, Vol 58, p 127, 2001], and dementia [*Exp. Opin. Invest. Drugs*, Vol 9, p 671, 2000].

In addition, it is anticipated that selective COX-2 inhibitors would be effective in treating osteoporosis and glaucoma. Utility of selective COX-2 inhibitors is well described in documents [John Vane, "Towards a Better Aspirin" in *Nature*, Vol. 367, pp 215–216, 1994; Bruno Battistini, Regina Botting and Y. S. Bakhle, "COX-1 and COX-2: Toward the Development of More Selective NSAIDs" in *Drug News and Perspectives*, Vol. 7, pp 501–512, 1994; David B. Reitz and Karen Seibert, "Selective Cyclooxygenase Inhibitors" in *Annual Reports in Medicinal Chemistry*, James A. Bristol, Editor, Vol. 30, pp 179–188, 1995].

Various selective COX-2 inhibitors having different structures have been known. Among them, a selective COX-2 inhibitor having a diaryl heterocyclic structure, i.e. a tricyclic structure has been widely studied as a potent candidate. The diaryl heterocyclic structure has a central ring and a sulfonamide or methylsulfone group attached to one of the aryl rings. An initial substance having such diaryl heterocyclic structure is Dup697 [*Bioorganic & Medicinal Chemistry Letters*, Vol 5, p 2123, 1995]. Since then, SC-58635 having a pyrazol ring (*Journal of Medicinal Chemistry*, Vol 40, p 1347, 1997) and MK-966 having a furanone ring (WO 95/00501) were discovered as derivatives of the Dup697.

One selective COX-2 inhibitor, Celecoxib of formula 58 is disclosed in U.S. Pat. No. 5,466,823. The Celecoxib is a substituted pyrazolyl benzenesulfonamide derivative.

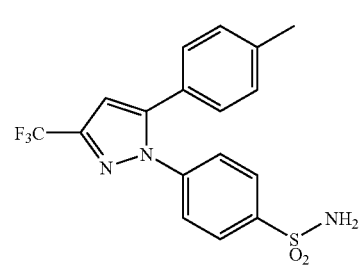

Formula 58

Another selective COX-2 inhibitor, Rofecoxib of formula 59 is disclosed in WO 95/00501. The Rofecoxib has a diaryl heterocyclic structure with a central furanone ring.

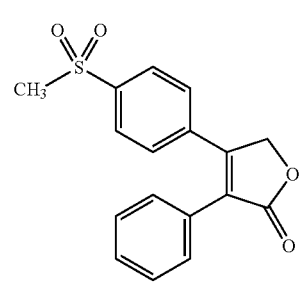

Formula 59

Valdecoxib of formula 60 as another selective COX-2 inhibitor is disclosed in U.S. Pat. No. 5,633,272. The Valdecoxib has a phenylsulfonamide moiety with a central isoxazole ring.

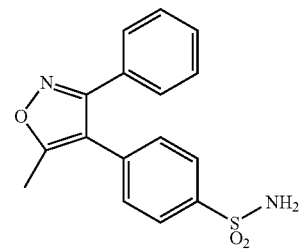

Formula 60

The selective COX-2 inhibitors of formulas 58 to 60 are effective inflammatory therapeutic agents with fewer and less side effects in comparison with conventional nonsteroidal antiinflammatory agents.

SUMMARY OF THE INVENTION

An object of the present invention is to provide a 1,2,4-triazole derivative of formula 1 or a non-toxic salt thereof.

Another object of the present invention is to provide a method for preparing a 1,2,4-triazole derivative or a non-toxic salt thereof.

Another object of the present invention is to provide pharmaceutical compositions comprising a 1,2,4-triazole derivative or a non-toxic salt thereof as an active ingredient for the treatment of fever, pain, and inflammation.

Yet another object of the present invention is to provide a pharmaceutical composition comprising a 1,2,4-triazole derivative or a non-toxic salt thereof as an active ingredient for the treatment of cancers and dementia.

DETAILED DESCRIPTION OF THE INVENTION

According to an aspect of the present invention, there is provided 1,2,4-triazole derivatives represented by formula 1:

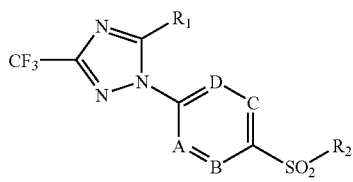

Formula 1 wherein:

$R_1$ is a $C_3$–$C_6$ cycloalkyl group; a $C_3$–$C_6$ cycloalkenyl group; a phenyl group; a phenyl group substituted with one or more selected from the group consisting of a $C_1$–$C_6$ alkyl group, a $C_1$–$C_6$ haloalkyl group, a $C_1$–$C_6$ alkoxy group, a $C_1$–$C_6$ haloalkoxy group, a halogen group, an amino group, a monoalkylamino group, a dialkylamino group, a nitro group, and a cyano group; a styrenyl group; a $C_1$–$C_6$ alkoxy styrenyl group; or a pyridyl group;

$R_2$ is a methyl or amino group; and

A, B, C, and D are independently carbon or nitrogen;

or a non-toxic salt thereof.

The 1,2,4-triazole derivative of formula 1 may be present in the form of a non-toxic salt. The term, "non-toxic salt" as used herein refers to a pharmaceutically acceptable, toxin-free salt, including an organic salt and an inorganic salt.

The Inorganic salt of the 1,2,4-triazole derivative of formula 1 includes an inorganic salt of aluminum, ammonium, calcium, copper, iron, lithium, magnesium, manganese, potassium, sodium, or zinc but is not limited thereto. An inorganic salt of ammonium, calcium, potassium, or sodium is preferable.

The organic salt of the 1,2,4-triazole derivative of formula 1 includes an organic amine salt of primary, secondary, or tertiary amine, substituted amine that is present in nature, or cyclic amine, or a salt of a basic ion exchange resin but is not limited thereto. Examples of the salt of a basic ion exchange resin include, but are not limited to, a salt of arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, N-methylglucamine, glucamine, glucosamine, histidine, N-(2-hydroxyethyl)piperidine, N-(2-hydroxyethyl)pyrrolidine, isopropylamine, lysine, methylglucamine, morpholine, piperazine, piperidine, polyamine resin, procaine, purine, triethylamine, trimethylamine, and tripropylamine.

The 1,2,4-triazole derivative of formula 1 may be present in the form of an organic acid salt or an inorganic acid salt.

Examples of the organic acid salt or the inorganic acid salt of the 1,2,4-triazole derivative of formula 1 include, but are not limited to, a salt of acetic acid, adipic acid, aspartic acid, 1,5-naphthalene disulfonic acid, benzene sulfonic acid, benzoic acid, camphor sulfonic acid, citric acid, 1,2-ethane disulfonic acid, ethane sulfonic acid, ethylenediaminetetraacetic acid, fumaric acid, glucoheptonic acid, gluconic acid, glutamic acid, hydroiodic acid, hydrobromic acid, hydrochloric acid, isethionic acid, lactic acid, maleic acid, malic acid, mandelic acid, methane sulfonic acid, mucic acid, 2-naphthalenedisulfonic acid, nitric acid, oxalic acid, pentothenic acid, phosphoric acid, pivalric acid, propionic acid, salicylic acid, stearic acid, succinic acid, sulfuric acid, tartaric acid, p-toluene sulfonic acid, undecanoic acid, and 10-undecenoic acid. A salt of succinic acid, hydrobromic acid, hydrochloric acid, maleic acid, methanesulfonic acid, phosphoric acid, sulfuric acid, or tartaric acid is preferable.

A preferred group of the 1,2,4-triazole derivative of the present invention is as follows:

1-(4-methanesulfonylphenyl)-5-phenyl-3-trifluoromethyl-1 H-[1,2,4]triazole;

5-(4-bromophenyl)-1-(4-methanesulfonylphenyl)-3-trifluoromethyl-1H-[1,2,4]triazole;

5-(3-bromophenyl)-1-(4-methanesulfonylphenyl)-3-trifluoromethyl-1H-[1,2,4]triazole;

5-(4-fluorophenyl )-1-(4-methanesulfonylphenyl)-3-trifluoromethyl-1H-[1,2,4]triazole;

5-(3,5-dichloro-4-methoxyphenyl)-1-(4-methanesulfonylphenyl)-3-trifluoromethyl-1H-[1,2,4]triazole;

5-(4-chlorophenyl)-1-(4-methanesulfonyl phenyl)-3-trifluoromethyl-1H-[1,2,4]triazole;

5-(3,4-dichlorophenyl)-1-(4-methanesulfonylphenyl)-3-trifluoromethyl-1H-[1,2,4]triazole;

5-(3,4-dimethoxyphenyl)-1-(4-methanesulfonylphenyl)-3-trifluoromethyl-1H-[1,2,4]triazole;

5-(3,4-difluorophenyl)-1-(4-methanesulfonylphenyl)-3-trifluoromethyl-1H-[1,2,4]triazole;

1-(4-methanesulfonylphenyl)-5-(4-methoxyphenyl)-3-trifluoromethyl-1H-[1,2,4]triazole;

5-(3,4-dimethoxyphenyl)-1-(4-methanesulfonylphenyl)-3-trifluoromethyl-1H-[1,2,4]triazole;

1-(4-methanesulfonylphenyl)-5-p-tolyl-3-trifluoromethyl-1H-[1,2,4]triazole;

5-(3,4-dimethylphenyl)-1-(4-methanesulfonylphenyl)-3-trifluoromethyl-1H-[1,2,4]triazole;

5-(3-chloro-4-methylphenyl)-1-(4-methanesulfonylphenyl)-3-trifluoromethyl-1H-[1,2,4]triazole;

5-(4-chloro-3-methylphenyl)-1-(4-methanesulfonylphenyl)-3-trifluoromethyl-1H-[1,2,4]triazole;

5-(3-chloro-4-methoxyphenyl)-1-(4-methanesulfonylphenyl)-3-trifluoromethyl-1H-[1,2,4]triazole;

5-(4-chloro-3-methoxyphenyl)-1-(4-methanesulfonylphenyl)-3-trifluoromethyl-1H-[1,2,4]triazole;

5-(3-fluoro-4-methylphenyl)-1-(4-methanesulfonylphenyl)-3-trifluoromethyl-1H-[1,2,4]triazole;

5-(4-fluoro-3-methylphenyl)-1-(4-methanesulfonylphenyl)-3-trifluoromethyl-1H-[1,2,4]triazole;

5-(3-fluoro-4-methoxyphenyl)-1-(4-methanesulfonylphenyl)-3-trifluoromethyl-1H-[1,2,4]triazole;

1-(4-methanesulfonylphenyl)-3-trifluoromethyl-5-(4-trifluoromethylphenyl)-1H-[1,2,4]triazole;

5-(4-ethoxyphenyl)-1-(4-methanesulfonylphenyl)-3-trifluoromethyl-1H-[1,2,4]triazole;

5-(4-methanesulfonylphenyl)-5-(4-trifluoromethoxyphenyl)-3-trifluoromethyl-1H-[1,2,4]triazole;

5-(4-t-butylphenyl)-1-(4-methanesulfonylphenyl)-3-trifluoromethyl-1H-[1,2,4]triazole;

5-(4-cyanophenyl)-1-(4-methanesulfonylphenyl)-3-trifluoromethyl-1H-[1,2,4]triazole;

5-[4-(N-methylamino)-phenyl]-1-(4-methanesulfonylphenyl)-3-trifluoromethyl-1H-[1,2,4]triazole;

5-[4-(N,N-dimethylamino)-phenyl]-1-(4-methanesulfonylphenyl)-3-trifluoromethyl-1H-[1,2,4]triazole;

5-(4-aminophenyl)-1-(4-methanesulfonylphenyl)-3-trifluoromethyl-1H-[1,2,4]triazole;

5-(3-trifluoromethylphenyl)-1-(4-methanesulfonylphenyl)-3-trifluoromethyl-1H-[1,2,4]triazole;

5-(3-methoxyphenyl)-1-(4-methanesulfonylphenyl)-3-trifluoromethyl-1H-[1,2,4]triazole;

1-(4-methanesulfonylphenyl)-5-m-tolyl-3-trifluoromethyl-1H-[1,2,4]triazole;

1-(4-methanesulfonylphenyl)-5-o-tolyl-3-trifluoromethyl-1H-[1,2,4]triazole;

5-(2-bromophenyl)-1-(4-methanesulfonylphenyl)-3-trifluoromethyl-1H-[1,2,4]triazole;

5-(2-methoxyphenyl)-1-(4-methanesulfonylphenyl)-3-trifluoromethyl-1H-[1,2,4]triazole;

5-(2,4-difluorophenyl)-1-(4-methanesulfonylphenyl)-3-trifluoromethyl-1H-[1,2,4]triazole;

5-(2,5-difluorophenyl)-1-(4-methanesulfonylphenyl)-3-trifluoromethyl-1H-[1,2,4]triazole;

5-(2,4,5-trifluorophenyl)-1-(4-methanesulfonylphenyl)-3-trifluoromethyl-1H-[1,2,4]triazole;

5-(2,3-dichlorophenyl)-1-(4-methanesulfonylphenyl)-3-trifluoromethyl-1H-[1,2,4]triazole;

5-(2,4-dichlorophenyl)-1-(4-methanesulfonylphenyl)-3-trifluoromethyl-1H-[1,2,4]triazole;

5-(3,5-difluorophenyl)-1-(4-methanesulfonylphenyl)-3-trifluoromethyl-1H-[1,2,4]triazole;

5-(3,5-dimethoxyphenyl)-1-(4-methanesulfonylphenyl)-3-trifluoromethyl-1H-[1,2,4]triazole;

5-(2,4-dimethoxyphenyl)-1-(4-methanesulfonylphenyl)-3-trifluoromethyl-1H-[1,2,4]triazole;

5-(3,4,5-trimethoxyphenyl)-1-(4-methanesulfonylphenyl)-3-trifluoromethyl-1H-[1,2,4]triazole;

5-(2-fluoro-4-trifluoromethylphenyl)-1-(4-methanesulfonylphenyl)-3-trifluoromethyl-1H-[1,2,4]triazole;

5-(2-chloro-4-nitrophenyl)-1-(4-methanesulfonylphenyl)-3-trifluoromethyl-1H-[1,2,4]triazole;

5-(2,4-dichloro-5-fluorophenyl)-1-(4-methanesulfonylphenyl)-3-trifluoromethyl-1H-[1,2,4]triazole;

5-(3-fluoro-4-methylphenyl)-1-(4-methanesulfonylphenyl)-3-trifluoromethyl-1H-[1,2,4]triazole;

5-benzo[1,3]dioxol-5-yl-1-(4-methanesulfonylphenyl)-3-trifluoromethyl-1H-[1,2,4]triazole;

5-methanesufonyl-2-[3-trifluoromethyl-5-(trifluoromethylpheny)-[1,2,4]triazole-1-yl]pyridine;

5-methanesulfonyl-2-[3-trifluoromethyl-5-(4-ethoxyphenyl)-[1,2,4]triazol-1-yl]pyridine;

5-methanesulfonyl-2-[3-trifluoromethyl-5-(4-trifluoromethoxyphenyl)-[1,2,4]triazol-1-yl]pyridine;

5-methanesulfonyl-2-[3-trifluoromethyl-5-(4-t-butylphenyl)-[1,2,4]triazol-1-yl]pyridine;

5-methanesulfonyl-2-[3-trifluoromethyl-5-(4-cyanophenyl)-[1,2,4]triazol-1-yl]pyridine;

5-methanesulfonyl-2-[3-trifluoromethyl-5-(4-aminophenyl)-[1,2,4]triazol-1-yl]pyridine;

5-methanesulfonyl-2-[3-trifluoromethyl-5-(4-N-methylaminophenyl)-[1,2,4]triazol-1-yl]pyridine;

5-methanesulfonyl-2-[3-trifluoromethyl-5-(4-N,N-dimethylaminophenyl)-[1,2,4]triazol-1-yl]pyridine;

5-methanesulfonyl-2-[3-trifluoromethyl-5-(3-methylphenyl)-[1,2,4]triazol-1-yl]pyridine;

5-methanesulfonyl-2-[3-trifluoromethyl-5-(3-trifluoromethylphenyl)-[1,2,4]triazol-1-yl]pyridine;

5-methanesulfonyl-2-3-trifluoromethyl-5-(3-methoxyphenyl)-[1,2,4]triazol-1-yl]pyridine;

5-methanesulfonyl-2-[3-trifluoromethyl-5-(2,4-difluorophenyl)-[1,2,4]triazol-1-yl]pyridine;

5-methanesulfonyl-2-[3-trifluoromethyl-5-(2,5-difluorophenyl)-[1,2,4]triazol-1-yl]pyridine;

5-methanesulfonyl-2-[3-trifluoromethyl-5-(2,4,5-trifluorophenyl)-[1,2,4]triazol-1-yl]pyridine;

5-methanesulfonyl-2-[3-trifluoromethyl-5-(2,3-dichlorophenyl)-[1,2,4]triazol-1-yl]pyridine;

5-methanesulfonyl-2-[3-trifluoromethyl-5-(2,4-dichlorophenyl)-[1,2,4]triazol-1-yl]pyridine;

5-methanesulfonyl-2-[3-trifluoromethyl-5-(3,5-difluorophenyl)-[1,2,4]triazol-1-yl]pyridine;

5-methanesulfonyl-2-[3-trifluoromethyl-5-(3,5-dimethoxyphenyl)-[1,2,4]triazol-1-yl]pyridine;

5-methanesulfonyl-2-[3-trifluoromethyl-5-(2,4-dimethoxyphenyl)-[1,2,4]triazol-1-yl]pyridine;

5-methanesulfonyl-2-[3-trifluoromethyl-5-(3,4,5-trifluorophenyl)-[1,2,4]triazol-1-yl]pyridine;

5-methanesulfonyl-2-[3-trifluoromethyl-5-(2-fluoro-4-trifluoromethylphenyl)-[1,2,4]triazol-1-yl]pyridine;

5-methanesulfonyl-2-[3-trifluoromethyl-5-(2-chloro-4-nitrophenyl)-[1,2,4]triazol-1-yl]pyridine;

5-methanesulfonyl-2-[3-trifluoromethyl-5-(2,4-dichloro-5-fluorophenyl)-[1,2,4]triazol-1-yl]pyridine;

5-methanesulfonyl-2-[3-trifluoromethyl-5-(3-fluoro-4-methylphenyl)-[1,2,4]triazol-1-yl]pyridine;

2-(5-benzo[1,3]dioxol-5-yl-3-trifluoromethyl-[1,2,4]triazol-1-yl)-5-methanesulfonyl pyridine;

3-[2-(4-methanesulfonylphenyl)-5-trifluoromethyl-2H-[1,2,4]triazol-3-yl]pyridine;

4-[2-(4-methanesulfonylphenyl)-5-trifluoromethyl-2H-[1,2,4]triazol-3-yl]pyridine;

5-cyclohexyl-1-(4-methanesulfonylphenyl)-3-trifluoromethyl-1H-[1,2,4]triazole;

5-cyclohexen-1-yl-1-(4-methanesulfonylphenyl)-3-trifluoromethyl-1H-[1,2,4]triazole;

4-(5-phenyl-3-trifluoromethyl-[1,2,4]triazol-1-yl)benzenesulfonamide;

4-[5-(4-bromophenyl)-3-trifluoromethyl-[1,2,4]triazol-1-yl]benzenesulfonamide;

4-[5-(4-fluorophenyl)-3-trifluoromethyl-[1,2,4]triazol-1-yl]benzenesulfonamide;

4-[5-(3,4-difluorophenyl)-3-trifluoromethyl-[1,2,4]triazol-1-yl]benzenesulfonamide;

4-[5-(4-chlorophenyl)-3-trifluoromethyl-[1,2,4]triazol-1-yl]benzenesulfonamide;

4-[5-(3,4-dichlorophenyl)-3-trifluoromethyl-[1,2,4]triazol-1-yl]benzenesulfonamide;

4-[5-(4-methoxyphenyl)-3-trifluoromethyl-[1,2,4]triazol-1-yl]benzenesulfonamide;

4-[5-(3,4-dimethoxyphenyl)-3-trifluoromethyl-[1,2,4]triazol-1-yl]benzenesulfonamide;

4-(5-p-tolyl-3-trifluoromethyl-[1,2,4]triazol-1-yl)benzenesulfonamide;

4-[5-(3,4-dimethylphenyl)-3-trifluoromethyl-[1,2,4]triazol-1-yl]benzenesulfonamide;

4-[5-(3-chloro-4-methylphenyl)-3-trifluoromethyl-[1,2,4]triazol-1-yl]benzenesulfonamide;

4-[5-(4-chloro-3-methylphenyl)-3-trifluoromethyl-[1,2,4]triazol-1-yl]benzenesulfonamide;

4-[5-(3-chloro-4-methoxyphenyl)-3-trifluoromethyl-[1,2,4]triazol-1-yl]benzenesulfonamide;

4-[5-(4-chloro-3-methoxyphenyl )-3-trifluoromethyl-[1,2,4]triazol-1-yl]benzenesulfonamide;

4-[5-(3-fluoro-4-methylphenyl)-3-trifluoromethyl-[1,2,4]triazol-1-yl]benzenesulfonamide;

4-[5-(4-fluoro-3-methylphenyl)-3-trifluoromethyl-[1,2,4]triazol-1-yl]benzenesulfonamide;

4-[5-(3-fluoro-4-methoxyphenyl)-3-trifluoromethyl-[1,2,4]triazol-1-yl]benzenesulfonamide;

4-[5-(3,5-dichloro-4-methoxyphenyl)-3-trifluoromethyl-[1,2,4]triazol-1-yl]benzenesulfonamide;

4-[3-trifluoromethyl-5-(4-trifluoromethylphenyl)-[1,2,4]triazol-1-yl]benzenesulfonamide;

4-[3-trifluoromethyl-5-(4-ethoxyphenyl)-[1,2,4]triazol-1-yl]benzenesulfonamide;

4-[3-trifluoromethyl-5-(4-trifluoromethoxyphenyl)-[1,2,4]triazol-1-yl]benzenesulfonamide;

4-[3-trifluoromethyl-5-(4-t-butylphenyl)-[1,2,4]triazol-1-yl]benzenesulfonamide;

4-[3-trifluoromethyl-5-(4-cyanophenyl)-[1,2,4]triazol-1-yl]benzenesulfonamide;

4-[3-trifluoromethyl-5-(4-aminophenyl)-[1,2,4]triazol-1-yl]benzenesulfonamide;

4-[3-trifluoromethyl-5-(4-N-methylaminophenyl)-[1,2,4]triazol-1-yl]benzenesulfonamide;

4-[3-trifluoromethyl-5-(4-N,N-dimethylaminophenyl)-[1,2,4]triazol-1-yl]benzenesulfonamide;

4-[3-trifluoromethyl-5-m-tolyl-[1,2,4]triazol-1-yl]benzenesulfonamide;

4-[3-trifluoromethyl-5-(3-trifluoromethylphenyl)-[1,2,4]triazol-1-yl]benzenesulfonamide;

4-[3-trifluoromethyl-5-(3-methoxyphenyl)-[1,2,4]triazol-1-yl]benzenesulfonamide;

4-[3-trifluoromethyl-5-(2-bromophenyl)-[1,2,4]triazol-1-yl]benzenesulfonamide;

4-[3-trifluoromethyl-5-(2-methoxyphenyl )-[1,2,4]triazol-1-yl]benzenesulfonamide;

4-[3-trifluoromethyl-5-(2,4-difluorophenyl)-[1,2,4]triazol-1-yl]benzenesulfonamide;

4-[3-trifluoromethyl-5-(2,5-difluorophenyl)-[1,2,4]triazol-1-yl]benzenesulfonamide;

4-[3-trifluoromethyl-5-(2,4,5-trifluorophenyl)-[1,2,4]triazol-1-yl]benzenesulfonamide;

4-[3-trifluoromethyl-5-(2,3-dichlorophenyl)-[1,2,4]triazol-1-yl]benzenesulfonamide;

4-[3-trifluoromethyl-5-(2,4-dichlorophenyl)-[1,2,4]triazol-1-yl]benzenesulfonamide;

4-[3-trifluoromethyl-5-(3,5-dimethoxyphenyl)-[1,2,4]triazol-1-yl]benzenesulfonamide;

4-[3-trifluoromethyl-5-(2,4-dimethoxyphenyl)-[1,2,4]triazol-1-yl]benzenesulfonamide;

4-[3-trifluoromethyl-5-(3,4,5-trifluorophenyl)-[1,2,4]triazol-1-yl]benzenesulfonamide;

4-[3-trifluoromethyl-5-(2-fluoro-4-trifluoromethylphenyl)-[1,2,4]triazol-1-yl]benzenesulfonamide;

4-[3-trifluoromethyl-5-(2-chloro-4-nitrophenyl)-[1,2,4]triazol-1-yl]benzenesulfonamide;

4-[3-trifluoromethyl-5-(2,4-dichloro-5-fluorophenyl)-[1,2,4]triazol-1-yl]benzenesulfonamide;

4-[3-trifluoromethyl-5-(3-fluoro-4-methylphenyl)-[1,2,4]triazol-1-yl]benzenesulfonamide;

4-(5-benzo[1,3]dioxol-5-yl-3-trifluoromethyl-[1,2,4]triazol-1-yl)benzenesulfonamide;

4-(5-pyridine-3-yl-3-trifluoromethyl-[1,2,4]triazol-1-yl)benzenesulfonamide;

4-(5-pyridin-4-yl-3-trifluoromethyl-[1,2,4]triazol-1-yl)benzenesulfonamide;

4-(5-cyclohexyl-3-trifluoromethyl-[1,2,4]triazol-1-yl)benzenesulfonamide;

4-(5-cyclohexen-1-yl-3-trifluoromethyl-[1,2,4]triazol-1-yl)benzenesulfonamide;

5-methanesulfonyl-2-(5-phenyl-3-trifluoromethyl-[1,2,4]triazol-1-yl)pyridine;

2-[5-(4-bromophenyl)-3-trifluoromethyl-[1,2,4]triazol-1-yl]-5-methanesulfonyl pyridine;

2-[5-(4-fluorophenyl)-3-trifluoromethyl-[1,2,4]triazol-1-yl]-5-methanesulfonyl pyridine;

2-[5-(3,4-difluorophenyl)-3-trifluoromethyl-[1,2,4]triazol-1-yl]-5-methanesulfonyl pyridine;

2-[5-(4-chlorophenyl)-3-trifluoromethyl-[1,2,4]triazol-1-yl]-5-methanesulfonyl pyridine;

2-[5-(3,4-dichlorophenyl)-3-trifluoromethyl-[1,2,4]triazol-1-yl]-5-methanesulfonyl pyridine;

5-methanesulfonyl-2-[5-(4-methoxyphenyl)-3-trifluoromethyl-[1,2,4]triazol-1-yl]pyridine;

2-[5-(3,4-dimethoxyphenyl)-3-trifluoromethyl-[1,2,4]triazol-1-yl]-5-methanesulfonyl pyridine;

5-methanesulfonyl-2-(5-p-tolyl-3-trifluoromethyl-[1,2,4]triazol-1-yl)pyridine;

2-[5-(3,4-dimethylphenyl)-3-trifluoromethyl-[1,2,4]triazol-1-yl]-5-methanesulfonyl pyridine;

2-[5-(3-chloro-4-methylphenyl)-3-trifluoromethyl-[1,2,4]triazol-1-yl]-5-methanesulfonyl pyridine;

2-[5-(4-chloro-3-methylphenyl)-3-trifluoromethyl-[1,2,4]triazol-1-yl]-5-methanesulfonyl pyridine;

6-[5-(3-chloro-4-methoxyphenyl)-3-trifluoromethyl-[1,2,4]triazol-1-yl]pyridine-3-sulfonic acid amide;

6-[5-(4-chloro-3-methoxyphenyl)-3-trifluoromethyl-[1,2,4]triazol-1-yl]pyridine-3-sulfonic acid amide;

6-[5-(3-fluoro-4-methylphenyl)-3-trifluoromethyl-[1,2,4]triazol-1-yl]pyridine-3-sulfonic acid amide;

6-[3-trifluoromethyl-5-(4-trifluoromethylphenyl)-[1,2,4]triazol-1-yl]pyridine-3-sulfonic acid amide;

6-[3-trifluoromethyl-5-(4-ethoxyphenyl)-[1,2,4]triazol-1-yl]pyridine-3-sulfonic acid amide;

6-[3-trifluoromethyl-5-(4-trifluoromethoxyphenyl)-[1,2,4]triazol-1-yl]pyridine-3-sulfonic acid amide;

6-[3-trifluoromethyl-5-(4-t-butylphenyl)-[1,2,4]triazol-1-yl]pyridine-3-sulfonic acid amide;

6-[3-trifluoromethyl-5-(4-cynophenyl)-[1,2,4]triazol-1-yl]pyridine-3-sulfonic acid amide;

6-[3-trifluoromethyl-5-(4-aminophenyl)-[1,2,4]triazol-1-yl]pyridine-3-sulfonic acid amide;

6-[3-trifluoromethyl-5-(4-N-methylaminophenyl)-[1,2,4]triazol-1-yl]pyridine-3-sulfonic acid amide;

6-[3-trifluoromethyl-5-(4-N,N-dimethylaminophenyl)-[1,2,4]triazol-1-yl]pyridine-3-sulfonic acid amide;

6-[3-trifluoromethyl-5-m-tolyl-[1,2,4]triazol-1-yl]pyridine-3-sulfonic acid amide;

6-[3-trifluoromethyl-5-(3-methoxyphenyl)-[1,2,4]triazol-1-yl]pyridine-3-sulfonic acid amide;

6-[3-trifluoromethyl-5-(3-trifluoromethylphenyl)-[1,2,4]triazol-1-yl]pyridine-3-sulfonic acid amide;

6-[3-trifluoromethyl-5-(2-bromophenyl)-[1,2,4]triazol-1-yl]pyridine-3-sulfonic acid amide;
6-[3-trifluoromethyl-5-(2-methoxyphenyl)-[1,2,4]triazol-1-yl]pyridine-3-sulfonic acid amide;
6-[3-trifluoromethyl-5-(2,4-difluorophenyl)-[1,2,4]triazol-1-yl]pyridine-3-sulfonic acid amide;
6-[3-trifluoromethyl-5-(2,5-difluorophenyl)-[1,2,4]triazol-1-yl]pyridine-3-sulfonic acid amide;
6-[3-trifluoromethyl-5-(3,5-difluorophenyl)-[1,2,4]triazol-1-yl]pyridine-3-sulfonic acid amide;
6-[3-trifluoromethyl-5-(2,4,5-trifluorophenyl)-[1,2,4]triazol-1-yl]pyridine-3-sulfonic acid amide;
6-[3-trifluoromethyl-5-(2-fluoro-4-trifluoromethylphenyl)-[1,2,4]triazol-1-yl]pyridine-3-sulfonic acid amide;
6-[3-trifluoromethyl-5-(2,4-dimethoxyphenyl)-[1,2,4]triazol-1-yl]pyridine-3-sulfonic acid amide;
6-[3-trifluoromethyl-5-(3,4,5-trimethoxyphenyl)-[1,2,4]triazol-1-yl]pyridine-3-sulfonic acid amide;
6-[3-trifluoromethyl-5-(2-chloro-4-nitrophenyl)-[1,2,4]triazol-1-yl]pyridine-3-sulfonic acid amide;
6-[3-trifluoromethyl-5-(2,4-difluoro-5-fluorophenyl)-[1,2,4]triazol-1-yl]pyridine-3-sulfonic acid amide;
6-[3-trifluoromethyl-5-(3-fluoro-4-methylphenyl)-[1,2,4]triazol-1-yl]pyridine-3-sulfonic acid amide;
2-[5-(4-fluoro-3-methylphenyl)-3-trifluoromethyl-[1,2,4]triazol-1-yl]-5-methanesulfonyl pyridine;
2-[5-(3-fluoro-4-methoxyphenyl)-3-trifluoromethyl-[1,2,4]triazol-1-yl]-5-methanesulfonyl pyridine;
2-[5-(3,5-dichloro-4-methoxyphenyl)-3-trifluoromethyl-[1,2,4]triazol-1-yl]-5-methanesulfonyl pyridine;
5-methanesulfonyl-2-((3-pyridinyl)-3-trifluoromethyl-[1,2,4]triazol-1-yl))pyridine;
5-methanesulfonyl-2-((4-pyridinyl)-3-trifluoromethyl-[1,2,4]triazol-1-yl))pyridine;
2-(5-cyclohexyl-3-trifluoromethyl-[1,2,4]triazol-1-yl)-5-methanesulfonyl pyridine;
2-(5-cyclohexen-1-yl-3-trifluoromethyl-[1,2,4]triazol-1-yl)-5-methanesulfonyl pyridine;
6-(5-phenyl-3-trifluoromethyl-[1,2,4]triazol-1-yl)pyridine-3-sulfonic acid amide;
6-[5-(4-bromophenyl)-3-trifluoromethyl-[1,2,4]triazol-1-yl]pyridine-3-sulfonic acid amide;
6-[5-(4-fluorophenyl)-3-trifluoromethyl-[1,2,4]triazol-1-yl]pyridine-3-sulfonic acid amide;
6-[5-(3,4-difluorophenyl)-3-trifluoromethyl-[1,2,4]triazol-1-yl]pyridine-3-sulfonic acid amide;
6-[5-(4-chlorophenyl)-3-trifluoromethyl-[1,2,4]triazol-1-yl]pyridine-3-sulfonic acid amide;
6-[5-(3,4-dichlorophenyl)-3-trifluoromethyl-[1,2,4]triazol-1-yl]pyridine-3-sulfonic acid amide;
6-[5-(4-methoxyphenyl)-3-trifluoromethyl-[1,2,4]triazol-1-yl]pyridine-3-sulfonic acid amide;
6-[5-(3,4-dimethoxyphenyl)-3-trifluoromethyl-[1,2,4]triazol-1-yl]pyridine-3-sulfonic acid amide;
6-(5-p-tolyl-3-trifluoromethyl-[1,2,4]triazol-1-yl)pyridine-3-sulfonic acid amide;
6-[5-(3,4-dimethylphenyl)-3-trifluoromethyl-[1,2,4]triazol-1-yl]pyridine-3-sulfonic acid amide;
6-[5-(3-chloro-4-methylphenyl)-3-trifluoromethyl-[1,2,4]triazol-1-yl]pyridine-3-sulfonic acid amide;
6-[5-(4-chloro-3-methylphenyl)-3-trifluoromethyl-[1,2,4]triazol-1-yl]pyridine-3-sulfonic acid amide;
6-[5-(3-chloro-4-methoxyphenyl)-3-trifluoromethyl-[1,2,4]triazol-1-yl]pyridine-3-sulfonic acid amide;
6-[5-(4-chloro-3-methoxyphenyl)-3-trifluoromethyl-[1,2,4]triazol-1-yl]pyridine-3-sulfonic acid amide;
6-[5-(3-fluoro-4-methylphenyl)-3-trifluoromethyl-[1,2,4]triazol-1-yl]pyridine-3-sulfonic acid amide;
6-[5-(4-fluoro-3-methylphenyl)-3-trifluoromethyl-[1,2,4]triazol-1-yl]pyridine-3-sulfonic acid amide;
6-[5-(3-fluoro-4-methoxyphenyl)-3-trifluoromethyl-[1,2,4]triazol-1-yl]pyridine-3-sulfonic acid amide;
6-[5-(3,5-dichloro-4-methoxyphenyl)-3-trifluoromethyl-[1,2,4]triazol-1-yl]pyridine-3-sulfonic acid amide;
6-(5-pyridin-3-yl-3-trifluoromethyl-[1,2,4]triazol-1-yl)pyridine-3-sufonic acid amide;
6-(5-pyridin-4-yl-3-trifluoromethyl-[1,2,4]triazol-1-yl)pyridine-3-sufonic acid amide;
6-(5-cyclohexyl-3-trifluoromethyl-[1,2,4]triazol-1-yl)pyridine-3-sufonic acid amide;
6-(5-cyclohexen-1-yl-3-trifluoromethyl-[1,2,4]triazol-1-yl)pyridine-3-sufonic acid amide;
2-methanesulfonyl-5-(5-phenyl-3-trifluoromethyl-[1,2,4]triazol-1-yl)pyridine;
5-[5-(4-bromophenyl)-3-trifluoromethyl-[1,2,4]triazol-1-yl]-2-methanesulfonyl pyridine;
5-[5-(4-fluorophenyl)-3-trifluoromethyl-[1,2,4]triazol-1-yl]-2-methanesulfonyl pyridine;
5-[5-(3,4-difluorophenyl)-3-trifluoromethyl-[1,2,4]triazol-1-yl]-2-methanesulfonyl pyridine;
5-[5-(4-chlorophenyl)-3-trifluoromethyl-[1,2,4]triazol-1-yl]-2-methanesulfonyl pyridine;
5-[5-(3,4-dichlorophenyl)-3-trifluoromethyl-[1,2,4]triazol-1-yl]-2-methanesulfonyl pyridine;
2-methanesulfonyl-5-[5-(4-methoxyphenyl)-3-trifluoromethyl-[1,2,4]triazol-1-yl]pyridine;
5-[5-(3,4-dimethoxyphenyl)-3-trifluoromethyl-[1,2,4]triazol-1-yl]-2-methanesulfonyl pyridine;
2-methanesulfonyl-5-(5-p-tolyl-3-trifluoromethyl-[1,2,4]triazol-1-yl)pyridine;
5-[5-(3,4-dimethylphenyl)-3-trifluoromethyl-[1,2,4]triazol-1-yl]-2-methanesulfonyl pyridine;
5-[5-(3-chloro-4-methylphenyl)-3-trifluoromethyl-[1,2,4]triazol-1-yl]-2-methanesulfonyl pyridine;
5-[5-(4-chloro-3-methylphenyl)-3-trifluoromethyl-[1,2,4]triazol-1-yl]-2-methanesulfonyl pyridine;
5-[5-(3-chloro-4-methoxyphenyl)-3-trifluoromethyl-[1,2,4]triazol-1-yl]-2-pyridine-2-sulfonic acid amide;
5-[5-(4-chloro-3-methoxyphenyl)-3-trifluoromethyl-[1,2,4]triazol-1-yl]pyridine-2-sulfonic acid amide;
5-[5-(3-fluoro-4-methylphenyl)-3-trifluoromethyl-[1,2,4]triazol-1-yl]pyridine-2-sulfonic acid amide;
5-[5-(4-fluoro-3-methylphenyl)-3-trifluoromethyl-[1,2,4]triazol-1-yl]-2-methanesulfonyl pyridine;
5-[5-(3-fluoro-4-methoxyphenyl)-3-trifluoromethyl-[1,2,4]triazol-1-yl]-2-methanesulfonyl pyridine;
5-[5-(3,5-dichloro-4-methoxyphenyl)-3-trifluoromethyl-[1,2,4]triazol-1-yl]-2-methanesulfonyl pyridine;
5-(5-cyclohexyl-3-trifluoromethyl-[1,2,4]triazol-1-yl)-2-methanesulfonyl pyridine;
5-(5-cyclohexen-1-yl-3-trifluoromethyl-[1,2,4]triazol-1-yl)-2-methanesulfonyl pyridine;
5-(5-phenyl-3-trifluoromethyl-[1,2,4]triazol-1-yl)pyridine-2-sulfonic acid amide;
5-[5-(4-bromophenyl)-3-trifluoromethyl-[1,2,4]triazol-1-yl]pyridine-2-sulfonic acid amide;
5-[5-(4-fluorophenyl)-3-trifluoromethyl-[1,2,4]triazol-1-yl]pyridine-2-sulfonic acid amide;
5-[5-(3,4-difluorophenyl)-3-trifluoromethyl-[1,2,4]triazol-1-yl]pyridine-2-sulfonic acid amide;
5-[5-(4-chlorophenyl)-3-trifluoromethyl-[1,2,4]triazol-1-yl]pyridine-2-sulfonic acid amide;

5-[5-(3,4-dichlorophenyl)-3-trifluoromethyl-[1,2,4]triazol-1-yl]pyridine-2-sulfonic acid amide;
5-[5-(4-methoxyphenyl)-3-trifluoromethyl-[1,2,4]triazol-1-yl]pyridine-2-sulfonic acid amide;
5-[5-(3,4-dimethoxyphenyl)-3-trifluoromethyl-[1,2,4]triazol-1-yl]pyridine-2-sulfonic acid amide;
5-(5-p-tolyl-3-trifluoromethyl-[1,2,4]triazol-1-yl)pyridine-2-sulfonic acid amide;
5-[5-(3,4-dimethylphenyl)-3-trifluoromethyl-[1,2,4]triazol-1-yl]pyridine-2-sulfonic acid amide;
5-[5-(3-chloro-4-methylphenyl)-3-trifluoromethyl-[1,2,4]triazol-1-yl]pyridine-2-sulfonic acid amide;
5-[5-(4-chloro-3-methylphenyl)-3-trifluoromethyl-[1,2,4]triazol-1-yl]pyridine-2-sulfonic acid amide;
5-[5-(3-chloro-4-methoxyphenyl)-3-trifluoromethyl-[1,2,4]triazol-1-yl]pyridine-2-sulfonic acid amide;
5-[5-(4-chloro-3-methoxyphenyl)-3-trifluoromethyl-[1,2,4]triazol-1-yl]-pyridine-2-sulfonic acid amide;
5-[5-(3-fluoro-4-methylphenyl)-3-trifluoromethyl-[1,2,4]triazol-1-yl]pyridine-2-sulfonic acid amide;
5-[5-(4-fluoro-3-methylphenyl)-3-trifluoromethyl-[1,2,4]triazol-1-yl]pyridine-2-sulfonic acid amide;
5-[5-(3-fluoro-4-methoxyphenyl )-3-trifluoromethyl-[1,2,4]triazol-1-yl]pyridine-2-sulfonic acid amide;
5-[5-(3,5-dichloro-4-methoxyphenyl)-3-trifluoromethyl-[1,2,4]triazol-1-yl]pyridine-2-sulfonic acid amide;
5-(5-pyridin-3-yl-3-trifluoromethyl-[1,2,4]triazol-1-yl)pyridine-2-sulfonic acid amide;
5-(5-pyridin-4-yl-3-trifluoromethyl-[1,2,4]triazol-1-yl)pyridine-2-sulfonic acid amide;
5-(5-cylcohexyl-3-trifluoromethyl-[1,2,4]triazol-1-yl)pyridine-2-sulfonic acid amide;
5-(5-cyclohexen-1-yl-3-trifluoromethyl-[1,2,4]triazol-1-yl)pyridine-2-sulfonic acid amide;
3-methanesulfonyl-6-(5-phenyl-3-trifluoromethyl-[1,2,4]triazol-1-yl)pyridazine;
3-[5-(4-bromophenyl)-3-trifluoromethyl-[1,2,4]triazol-1-yl]-6-methanesulfonyl pyridazine;
3-[5-(4-fluorophenyl)-3-trifluoromethyl-[1,2,4]triazol-1-yl]-6-methanesulfonyl pyridazine;
3-[5-(3,4-difluorophenyl)-3-trifluoromethyl-[1,2,4]triazol-1-yl]-6-methanesulfonyl pyridazine;
3-[5-(4-chlorophenyl)-3-trifluoromethyl-[1,2,4]triazol-1-yl]-6-methanesulfonyl pyridazine;
3-[5-(3,4-dichlorophenyl)-3-trifluoromethyl-[1,2,4]triazol-1-yl]-6-methanesulfonyl pyridazine;
3-methanesulfonyl-6-[5-(4-methoxyphenyl)-3-trifluoromethyl-[1,2,4]triazol-1-yl]pyridazine;
3-[5-(3,4-dimethoxyphenyl)-3-trifluoromethyl-[1,2,4]triazol-1-yl]-6-methanesulfonyl pyridazine;
3-methanesulfonyl-6-(5-p-tolyl-3-trifluoromethyl-[1,2,4]triazol-1-yl)pyridazine;
3-[5-(3,4-dimethylphenyl)-3-trifluoromethyl-[1,2,4]triazol-1-yl]-6-methanesulfonyl pyridazine;
3-[5-(3-chloro-4-methylphenyl)-3-trifluoromethyl-[1,2,4]triazol-1-yl]-6-methanesulfonyl pyridazine;
3-[5-(4-chloro-3-methylphenyl)-3-trifluoromethyl-[1,2,4]triazol-1-yl]-6-methanesulfonyl pyridazine;
3-[5-(3-chloro-4-methoxyphenyl)-3-trifluoromethyl-[1,2,4]triazol-1-yl]-6-methanesulfonyl pyridazine;
3-[5-(4-chloro-3-methoxyphenyl)-3-trifluoromethyl-[1,2,4]triazol-1-yl]-6-methanesulfonyl pyridazine;
3-[5-(3-fluoro-4-methylphenyl)-3-trifluoromethyl-[1,2,4]triazol-1-yl]-6-methanesulfonyl pyridazine;
3-[5-(4-fluoro-3-methylphenyl)-3-trifluoromethyl-[1,2,4]triazol-1-yl]-6-methanesulfonyl pyridazine;
3-[5-(3-fluoro-4-methoxyphenyl)-3-trifluoromethyl-[1,2,4]triazol-1-yl]-6-methanesulfonyl pyridazine;
3-[5-(3,5-dichloro-4-methoxyphenyl)-3-trifluoromethyl-[1,2,4]triazol-1-yl]-6-methanesulfonyl pyridazine;
3-methanesulfonyl-6-(5-pyridin-3-yl-3-trifluoromethyl-[1,2,4]triazol-1-yl)pyridazine;
3-methanesulfonyl-6-(5-pyridin-4-yl-3-trifluoromethyl-[1,2,4]triazol-1-yl)pyridazine;
3-(5-cyclohexyl-3-trifluoromethyl-[1,2,4]triazol-1-yl)-6-methanesulfonyl pyridazine;
3-(5-cyclohexen-1-yl-3-trifluoromethyl-[1,2,4]triazol-1-yl)-6-methanesulfonyl pyridazine;
6-(5-phenyl-3-trifluoromethyl-[1,2,4]triazol-1-yl)pyridazine-3-sulfonic acid amide;
6-[5-(4-bromophenyl)-3-trifluoromethyl-[1,2,4]triazol-1-yl]pyridazine-3-sulfonic acid amide;
6-[5-(4-fluorophenyl)-3-trifluoromethyl-[1,2,4]triazol-1-yl]pyridazine-3-sulfonic acid amide;
6-[5-(3,4-difluorophenyl)-3-trifluoromethyl-[1,2,4]triazol-1-yl]pyridazine-3-sulfonic acid amide;
6-[5-(4-chlorophenyl)-3-trifluoromethyl-[1,2,4]triazol-1-yl]pyridazine-3-sulfonic acid amide;
6-[5-(3,4-dichlorophenyl)-3-trifluoromethyl-[1,2,4]triazol-1-yl]pyridazine-3-sulfonic acid amide;
6-[5-(4-methoxyphenyl)-3-trifluoromethyl-[1,2,4]triazol-1-yl]pyridazine-3-sulfonic acid amide;
6-[5-(3,4-dimethoxyphenyl)-3-trifluoromethyl-[1,2,4]triazol-1-yl]pyridazine-3-sulfonic acid amide;
6-(5-p-tolyl-3-trifluoromethyl-[1,2,4]triazol-1-yl)pyridazine-3-sulfonic acid amide;
6-[5-(3,4-dimethyphenyl)-3-trifluoromethyl-[1,2,4]triazol-1-yl]pyridazine-3-sulfonic acid amide;
6-[5-(3-chloro-4-methyl phenyl)-3-trifluoromethyl-[1,2,4]triazol-1-yl]pyridazine-3-sulfonic acid amide;
6-[5-(4-chloro-3-methylphenyl)-3-trifluoromethyl-[1,2,4]triazol-1-yl]pyridazine-3-sulfonic acid amide;
6-[5-(3-chloro-4-methoxyphenyl)-3-trifluoromethyl-[1,2,4]triazol-1-yl]pyridazine-3-sulfonic acid amide;
6-[5-(4-chloro-3-methoxyphenyl)-3-trifluoromethyl-[1,2,4]triazol-1-yl]pyridazine-3-sulfonic acid amide;
6-[5-(3-fluoro-4-methylphenyl)-3-trifluoromethyl-[1,2,4]triazol-1-yl]pyridazine-3-sulfonic acid amide;
6-[5-(4-fluoro-3-methylphenyl )-3-trifluoromethyl-[1,2,4]triazol-1-yl]pyridazine-3-sulfonic acid amide;
6-[5-(3-fluoro-4-methoxyphenyl)-3-trifluoromethyl-[1,2,4]triazol-1-yl]pyridazine-3-sulfonic acid amide;
6-[5-(3,5-dichloro-4-methoxyphenyl)-3-trifluoromethyl-[1,2,4]triazol-1-yl]pyridazine-3-sulfonic acid amide;
6-(5-pyridin-3-yl-3-trifluoromethyl-[1,2,4]triazol-1-yl)pyridazine-3-sulfonic acid amide;
6-(5-pyridin-4-yl-3-trifluoromethyl-[1,2,4]triazol-1-yl)pyridazine-3-sulfonic acid amide;
6-(5-cyclohexyl-3-trifluoromethyl-[1,2,4]triazol-1-yl)pyridazine-3-sulfonic acid amide;
6-(5-cyclohexen-1-yl-3-trifluoromethyl-[1,2,4]triazol-1-yl)pyridazine-3-sulfonic acid amide;
5-methanesulfonly-2-(5-phenyl-3-trifluoromethyl-[1,2,4]triazol-1-yl)pyrimidine;
2-[5-(4-bromophenyl)-3-trifluoromethyl-[1,2,4]triazol-1-yl]-5-methanesulfonyl pyrimidine;
2-[5-(4-fluorophenyl)-3-trifluoromethyl-[1,2,4]triazol-1-yl]-5-methanesulfonyl pyrimidine;
2-[5-(3,4-difluorophenyl)-3-trifluoromethyl-[1,2,4]triazol-1-yl]-5-methanesulfonyl pyrimidine;
2-[5-(4-chlorophenyl)-3-trifluoromethyl-[1,2,4]triazol-1-yl]-5-methanesulfonyl pyrimidine;

2-[5-(3,4-dichlorophenyl)-3-trifluoromethyl-[1,2,4]triazol-1-yl]-5-methanesulfonyl pyrimidine;

5-methanesulfonyl-2-[5-(4-methoxyphenyl)-3-trifluoromethyl-[1,2,4]triazol-1-yl]pyrimidine;

2-[5-(3,4-dimethoxyphenyl)-3-trifluoromethyl-[1,2,4]triazol-1-yl]-5-methanesulfonyl pyrimidine;

5-methanesulfonyl-2-(5-p-tolyl-3-trifluoromethyl-[1,2,4]triazol-1-yl)pyrimidine;

2-[5-(3,4-dimethylphenyl)-3-trifluoromethyl-[1,2,4]triazol-1-yl]-5-methanesulfonyl pyrimidine;

2-[5-(3-chloro-4-methylphenyl)-3-trifluoromethyl-[1,2,4]triazol-1-yl]-5-methanesulfonyl pyrimidine;

2-[5-(4-chloro-3-methylphenyl)-3-trifluoromethyl-[1,2,4]triazol-1-yl]-5-methanesulfonyl pyrimidine;

2-[5-(3-chloro-4-methoxyphenyl)-3-trifluoromethyl-[1,2,4]triazol-1-yl]-5-methanesulfonyl pyrimidine;

2-[5-(4-chloro-3-methoxyphenyl)-3-trifluoromethyl-[1,2,4]triazol-1-yl]-5-methanesulfonyl pyrimidine;

2-[5-(3-fluoro-4-methylphenyl)-3-trifluoromethyl-[1,2,4]triazol-1-yl]-5-methanesulfonyl pyrimidine;

2-(5-phenyl-3-trifluoromethyl-[1,2,4]triazol-1-yl)pyrimidine-5-sulfonic acid amide;

2-[5-(4-bromophenyl)-3-trifluoromethyl-[1,2,4]triazol-1-yl]pyrimidine-5-sulfonic acid amide;

2-[5-(4-fluorophenyl)-3-trifluoromethyl-[1,2,4]triazol-1-yl]pyrimidine-5-sulfonic acid amide;

2-[5-(3,4-difluorophenyl)-3-trifluoromethyl-[1,2,4]triazol-1-yl]pyrimidine-5-sulfonic acid amide;

2-[5-(4-chlorophenyl)-3-trifluoromethyl-[1,2,4]triazol-1-yl]pyrimidine-5-sulfonic acid amide;

2-[5-(3,4-dichlorophenyl)-3-trifluoromethyl-[1,2,4]triazol-1-yl]pyrimidine-5-sulfonic acid amide;

2-[5-(4-methoxyphenyl)-3-trifluoromethyl-[1,2,4]triazol-1-yl]pyrimidine-5-sulfonic acid amide;

2-[5-(3,4-dimethoxyphenyl)-3-trifluoromethyl-[1,2,4]triazol-1-yl]pyrimidine-5-sulfonic acid amide;

2-(5-p-tolyl-3-trifluoromethyl-[1,2,4]triazol-1-yl)pyrimidine-5-sulfonic acid amide;

2-[5-(3,4-dimethylphenyl)-3-trifluoromethyl-[1,2,4]triazol-1-yl]pyrimidine-5-sulfonic acid amide;

2-[5-(3-chloro-4-methylphenyl)-3-trifluoromethyl-[1,2,4]triazol-1-yl]pyrimidine-5-sulfonic acid amide;

2-[5-(4-chloro-3-methylphenyl)-3-trifluoromethyl-[1,2,4]triazol-1-yl]pyrimidine-5-sulfonic acid amide;

2-[5-(3-chloro-4-methoxyphenyl)-3-trifluoromethyl-[1,2,4]triazol-1-yl]pyrimidine-5-sulfonic acid amide;

2-[5-(4-chloro-3-methoxyphenyl)-3-trifluoromethyl-[1,2,4]triazol-1-yl]pyrimidine-5-sulfonic acid amide;

2-[5-(3-fluoro-4-methylphenyl )-3-trifluoromethyl-[1,2,4]triazol-1-yl]pyrimidine-5-sulfonic acid amide;

5-styryl-1-(4-methanesulfonylphenyl)-3-trifluoromethyl-1H-[1,2,4]triazole; or

5-[2-(4-methoxyphenyl)-vinyl]-1-(4-methanesulfonylphenyl)-3-trifluoromethyl-1 H-[1,2,4]triazole.

According to another aspect of the present invention, there is provided an amidrazone derivative as an intermediate for the synthesis of the 1,2,4-triazole derivative of formula 1, as represented by formula 4:

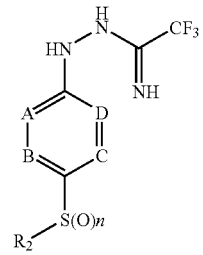

Formula 4 wherein, $R_2$, A, B, C, and D are as defined in formula 1 and n is an integer of 0 to 2.

According to another aspect of the present invention, there is provided a method for preparing a 1,2,4-triazole derivative of formula 1 or a non-toxic salt thereof, comprising reacting an amidrazone derivative of formula 4a with acyl chloride of formula 5 in the presence of base.

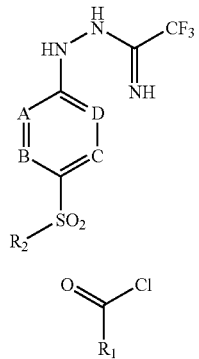

Formula 4a

Formula 5 wherein, $R_1$, $R_2$, A, B, C, and D are as defined in formula 1.

According to another aspect of the present invention, there is provided a method for preparing a 1,2,4-triazole derivative of formula 1 or a non-toxic salt thereof, comprising reacting an amidrazone derivative of formula 4b with acyl chloride of formula 5 in the presence of base and oxidizing the resultant compound with an oxidizing agent selected from the group consisting of magnesium monoperoxyphthalate hexahydrate (MMPP), m-chloroperoxybenzoic acid (MCPBA), and potassium peroxymonosulfate.

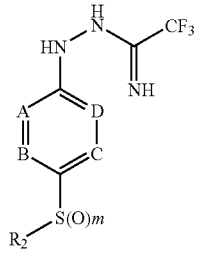

Formula 4b wherein, $R_2$, A, B, C, and D is as defined in formula 1 and m is 0 or 1.

The above mentioned reactions are preferably carried out in a polar solvent. Examples of the polar solvent include, but are not limited to, dimethylformamide, 1,4-dioxane, dimethylsulfoxide, N-methylpyrrolidinone, or m-xylene.

The reactions are preferably carried out at a temperature of −10 to 110° C. A reaction time is determined depending on reactants. Generally, a reaction time of 10 minutes to 36 hours is required.

When the reactions are completed, the reaction resultants are extracted with water and an organic solvent such as ethyl acetate, dichloromethane, tetrahydrofuran, and ether, to remove salts. The crude extracts are purified by silica gel column chromatography to give the final products.

Bases to be used herein are organic bases or inorganic bases. The preferred organic bases are triethyl amine, trimethyl amine, tripropyl amine, pyridine, or imidazole. The preferred inorganic bases are sodium acetate, sodium hydroxide, sodium hydride, potassium hydroxide, sodium carbonate, or potassium carbonate. Pyridine is the most preferred.

The oxidative reaction is preferably carried out in dichloromethane in the presence of an oxidizing agent. The preferred oxidizing agent is MMPP, MCPBA, or potassium peroxymonosulfate.

According to another aspect of the present invention, there is provided a method for preparing a compound of formula 1b, comprising reacting a compound of formula 1a with hydroxylamine or a salt thereof in the presence of a strong base and a Lewis acid.

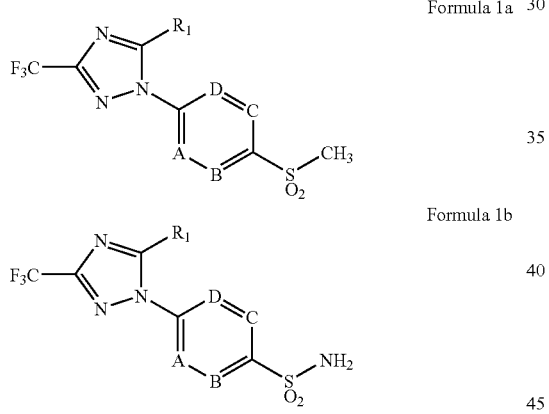

Formula 1a

Formula 1b wherein, $R_1$, A, B, C, and D are as defined in formula 1.

According to another aspect of the present invention, there is provided a method for preparing a 1,2,4-triazole derivative of formula 1b or a non-toxic salt thereof, comprising reacting a compound of formula 6a with hydroxylamine or a salt thereof in the presence of a strong base and a Lewis acid and oxidizing the resultant compound using an oxidizing agent selected from the group consisting of MMPP, MCPBA, and potassium peroxymonosulfate.

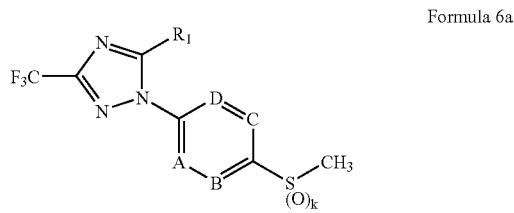

Formula 6a wherein, $R_1$, A, B, C, and D are as defined in formula 1 and k is 1 or 0.

The preferred hydroxylamine salt is hydroxylamine sulfate, hydroxylamine hydrochloride, hydroxylamine phosphate, hydroxylamine nitrate, or hydroxylamine sulfonate.

In order to prepare a compound in which $R_2$ is a amino group in formula 1, at first, a compound of formula 1a or a compound of formula 6a is dehydrogenated in a solvent of tetrahydrofuran or ether at −78 to 80° C. in the presence of a strong base of alkyl lithium, aryl lithium, alkyl magnesium chloride, or aryl magnesium chloride. Then, the resultant compound is reacted with a Lewis acid such as alkylboron, arylboron, alkylaluminium, and arylaluminium at −78 to 80° C., followed by amination using hydroxylamine sulfate. Preferably, hydroxylamine sulfate is used because when excess hydroxylamine sulfate is used, side reactions are minimal and the residual hydroxylamine sulfate and byproducts are easily removed upon extraction. After extraction, a crude extract is purified by column chromatography to produce a product having a desired sulfonamide group.

According to another aspect of the present invention, there is provided a method for preparing a compound of formula 4, comprising reacting a hydrazine derivative of formula 2 with trifluoroacetimidine of formula 3 in the presence of base.

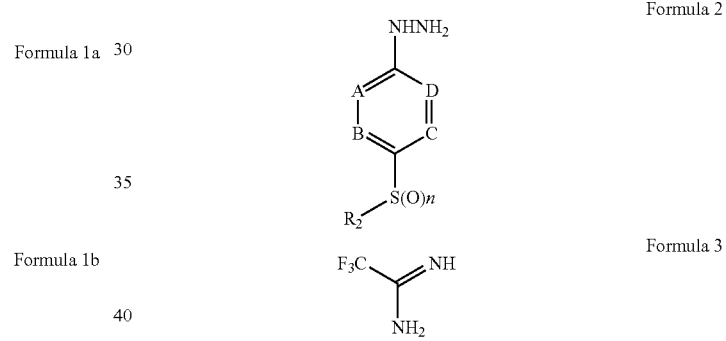

Formula 2

Formula 3 wherein, $R_2$, A, B, C, D, and n are as defined in formula 4.

The reaction is carried out in a solvent. The preferred solvent is methanol or a mixed solvent of methanol and tetrahydrofuran. The reaction is preferably carried out at a temperature of −10 to 66° C. A reaction time is determined depending on reactants. Preferably, the reaction time is 10 minutes to 48 hours.

When the reaction is completed, the reaction resultant is extracted with water and an organic solvent such as ethyl acetate, dichloromethane, tetrahydrofuran, and ether, to remove salts. The crude extract is purified by silica gel column chromatography to give the compound of formula 4.

The base to be used herein is an organic base or an inorganic base. Preferably, the organic base is triethyl amine, trimethyl amine, tripropyl amine, pyridine, or imidazole. Preferably, the inorganic base is sodium acetate, sodium hydroxide, sodium hydride, potassium hydroxide, sodium carbonate, or potassium carbonate. More preferably, triethylamine is used.

All crude products obtained from the above mentioned reactions are purified via a conventional post-treatment process, for example, chromatography and recrystallization to thereby give final products.

A method for preparing a compound of formula 1 is expressed by the following scheme 1:

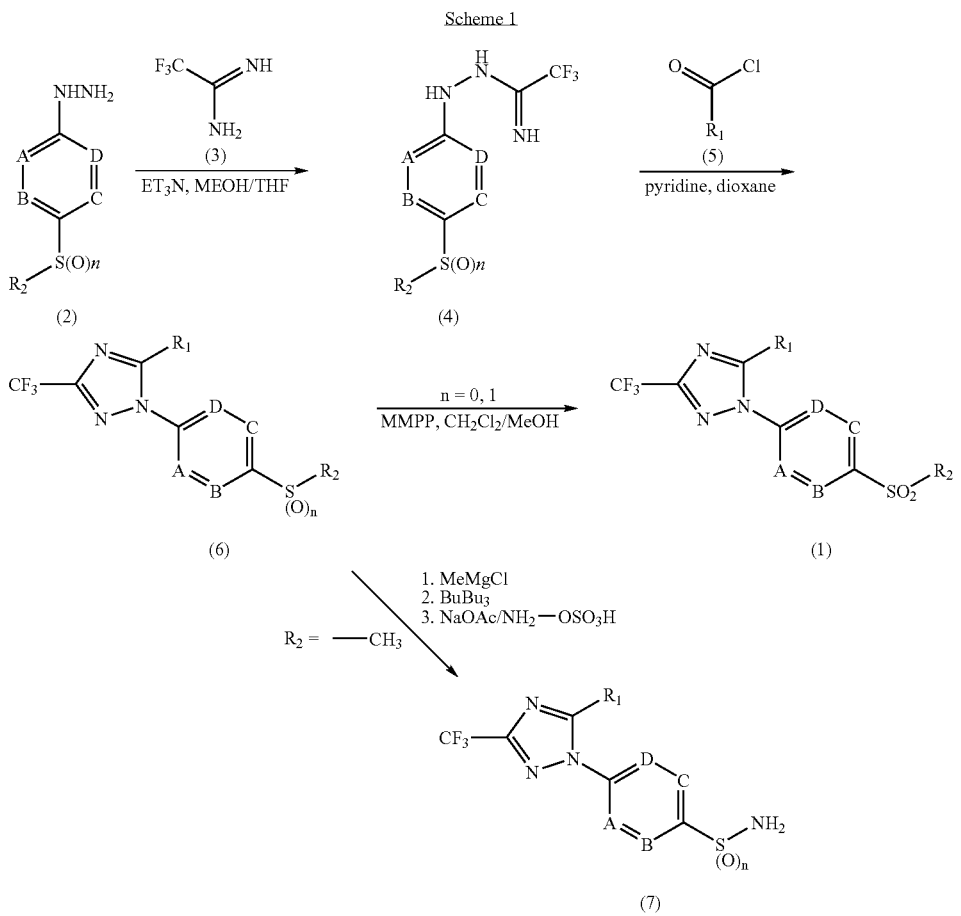

wherein, $R_1$, $R_2$, A, B, C, D, and n are as defined in the above.

As a hydrazine derivative to be used in the scheme 1, 4-hydrazinobenzenesulfonamide hydrochloride can be obtained from Maybridge (United Kingdom). Other hydrazine derivatives can be synthesized as it is or in the form of their hydrochlorides according to known methods [*Tetrahedron Letters*, vol 28, No 42, p 4933, 1987; U.S. Pat. No. 4,204,870; *The Journal of Organic Chemistry*, vol 56, No 16, p 4974, 1991; EP 1104759; and *Tetrahedron*, vol 48, No 21, p 6791, 1989]. The synthesis methods of representative hydrazine derivatives are presented in Schemes 2 to 5.

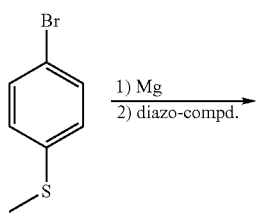

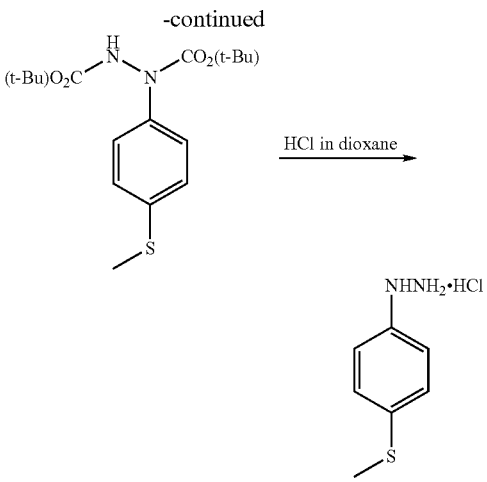

In Scheme 2, 4-bromo thioanisole is treated with magnesium to produce a Grignard compound. The Grignard compound reacts with a diazo compound and then hydrogen chloride to thereby produce a hydrochloride salt of hydrazine derivative.

Scheme 3

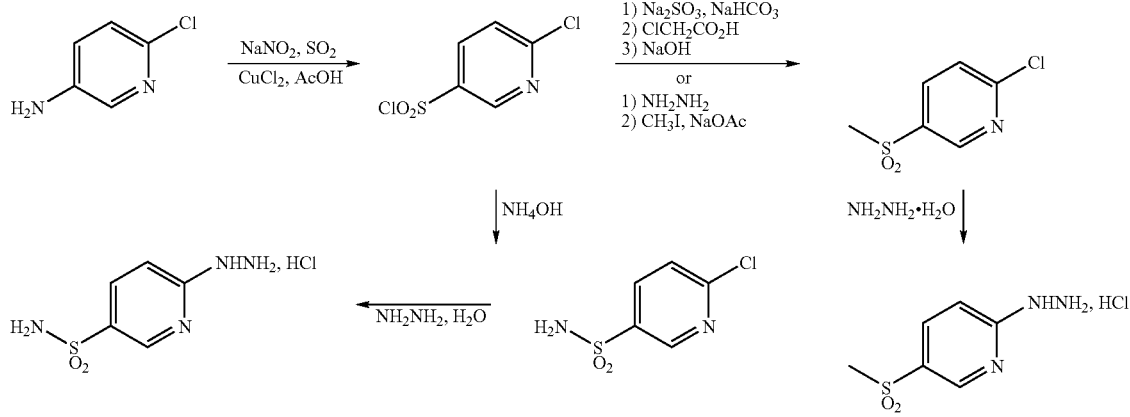

In Scheme 3, a pyridine derivative reacts with hydrazine monohydrate to produce a 2-hydrazinopyridine derivative.

Scheme 4

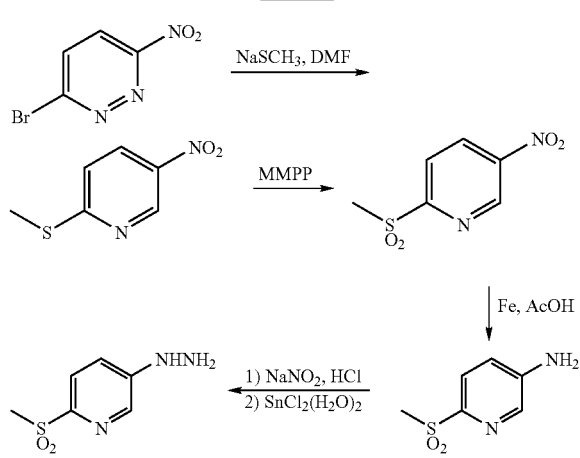

In Scheme 4, a nitro-substituted pyridine derivative is reduced to an amine-substituted pyridine derivative. Then, a hydrazine group is introduced to the amine-substituted pyridine derivative to produce a 3-hydrazinopyridine derivative.

Scheme 5

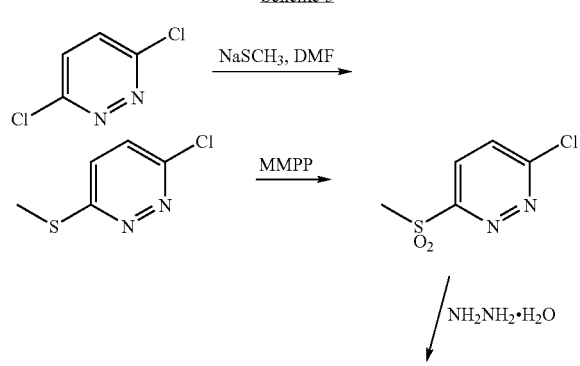

-continued

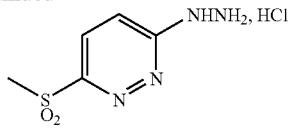

In Scheme 5, a 2-hydrazinopyridazine derivative is prepared from 2,5-dichloro pyridazine according to a similar method as in the scheme 3.

In methods for preparing compounds of the present invention, reaction conditions such as types and amounts of solvent, base, and reactants are not limited to those as mentioned in the above. It is understood that a person of ordinary skill in the art can easily prepare compounds of the present invention through any combination of synthesis methods as described in the specification or as disclosed in known documents.

According to another aspect of the present invention, there is provided a pharmaceutical composition comprising a therapeutically effective amount of a 1,2,4-triazol derivative or a non-toxic salt thereof as an active ingredient and a pharmaceutically acceptable carrier for the treatment of fever, pain, and inflammation.

The pharmaceutical composition comprises a compound of formula 1 or a non-toxic salt thereof when it is a selective inhibitor of cyclooxygenase-2. Therefore, the pharmaceutical composition can be used as an antipyretic, an analgesic, and an antiinflammatory agent, with minimal side effects.

Conventional nonsteroidal antiinflammatory agents nonselectively inhibit the prostaglandin synthesis enzymes, cyclooxygenase-1 and cyclooxygenase-2. Therefore, various side effects may occur.

On the other hand, a compound of formula 1 and a non-toxic salt thereof selectively inhibit cyclooxygenase-2. Therefore, the side effects of conventional nonsteroidal antipyretics, analgesics, and antiinflammatory agents can be reduced.

The pharmaceutical composition of the present invention comprises a compound of formula 1 and/or a non-toxic salt thereof and a pharmaceutically acceptable carrier or excipient. Therefore, the pharmaceutical composition may be used as a substitute for conventional nonsteroidal antiinflammatory agents. In particular, due to the reduction of the side effects of conventional nonsteroidal antipyretics, analgesics, and antiinflammatory agents, the pharmaceutical composition of the present invention is useful for treating patients with peptic ulcer, gastritis, regional enteritis, ulcerative colitis, diverticullitis, gastrorrhagia, or hypoprothrombinemia.

The pharmaceutical composition of the present invention can be used in all inflammatory diseases associated with pathological prostaglandin and is particularly appropriate for treating osteoarthritis and rheumatoid arthritis which require high dosage of nonsteroidal antiinflammatory agents.

The pharmaceutical composition of the present invention can be administered in the form of an adult dosage of 1 mg/day to 1000 mg/day of the compound of formula 1. An adequate dosage is determined depending on the degree of disease severity.

According to yet another aspect of the present invention, there is provided a pharmaceutical composition comprising a therapeutically effective amount of a 1,2,4-triazole derivative of formula 1 or a non-toxic salt thereof and a pharmaceutically acceptable carrier for the treatment of cancers and dementia.

Recently, it was reported that nonsteroidal antiinflammatory agents are effective for the treatment of large intestine cancer [*European Journal of Cancer*, Vol 37, p 2302, 2001], prostate cancer [*Urology*, Vol 58, p 127, 2001], and dementia [*Exp. Opin. Invest. Drugs*, Vol 9, p 671, 2000]. Therefore, it is understood that the pharmaceutical composition of the present invention as a nonsteroidal antiinflammatory agent can also be used for the treatment of these diseases.

The pharmaceutical composition of the present invention can be administered in the form of an adult dosage of 1 mg/day to 1000 mg/day of the compound of formula 1 or a non-toxic salt thereof. An adequate dosage is determined depending on the degree of disease severity.

The pharmaceutical composition of the present invention may be administered in the form of tablet, foam tablet, capsule, granule, powder, sustained-release tablet, sustained-release capsule (a single unit formulation or a multiple unit formulation), intravenous and intramuscular injectable solution, infusion solution, suspension, or suppository, or in other suitable dosage forms.

Sustained-release pharmaceutical dosage forms contain active ingredients with or without an initial loading dose. They are wholly or partially sustained-release pharmaceutical dosage forms to release active ingredients in a controlled manner.

Preferably, the pharmaceutical composition is orally administered.

The pharmaceutical composition further comprises a pharmaceutically acceptable excipient and/or diluent and/or adjuvant in pharmaceutically effective amounts.

Examples of the excipient and adjuvant include gellatin, a natural sugar such as sucrose and lactose, lecitin, pectin, starch such as corn starch and amylose, cyclodextrin and cyclodextrin derivative, dextran, polyvinylpyrrolidone, polyvinyl acetate, Arabic gum, arginic acid, xylose, talc, salicylic acid, calcium hydrogen phosphate, cellulose, cellulose derivative such as methylcellulose, methoxypropyl cellulose, hydroxypropylmethyl cellulose, and hydroxypropylmethylcellulose phthalate, fatty acid having 12 to 22 carbon atoms, emulsifying agent, oil and fat, in particular, vegetable glycerol ester and polyglycerol ester of saturated fatty acids, monohydric alcohol, polyhydric alcohol, polyglycol such as polyethylene glycol, aliphatic alcohol having 1 to 20 carbon atoms, or aliphatic saturated or unsaturated fatty acid ester having 2 to 22 carbon atoms with polyhydric alcohols such as glycol, glycerol, diethylene glycol, 1,2-propylene glycol, sorbitol, and mannitol.

Other suitable adjuvants include a disintegrating agent. Examples of the disintegrating agent include a cross-linked polyvinylpyrrolidone, sodium carboxymethyl starch, sodium carboxymethyl cellulose, and microcrystalline cellulose. A coating agent which is conventionally used in this field may also be used. Examples of the coating agent include acrylic acid and/or methacrylic acid and/or an ester polymer or copolymer thereof, zein, ethyl cellulose, ethyl cellulose succinate, and Shellac.

Plasticizers suitable for the coating agent are citric ester and tartaric ester, glycerol and glycerol ester, or polyethylene glycol with different chain lengths.

A liquid composition such as solution and suspension is formulated in water or a physiological acceptable organic solvent such as alcohol and aliphatic alcohol.

The liquid pharmaceutical composition may further comprise a preservative such as potassium solvate, methyl 4-hydroxybenzoate, and propyl 4-hydroxybenzoate, an antioxidant such as ascorbic acid, and a fragrant such as peppermint oil.

In addition, when the liquid pharmaceutical composition is formulated, a conventional solubilizer or emulsifier such as polyvinylpyrrolidone and polysolvate 80 may be used.

Other examples of suitable excipients and adjuvants are disclosed Dr. H. P. Fielder, "Lexikon der Hilfsstoffe fur Pharmazie, Kosmetik und angrenzende Gebiete" [Encyclopaedia of auxiliaries for pharmacy, cosmetics and related fields].

Hereinafter, the present invention will be described more specifically by examples. However, the following examples are provided only for illustrations and thus the present invention is not limited to or by them.

EXAMPLE 1

N-(4-methylsulfanylphenyl)trifluoroacetamidrazone

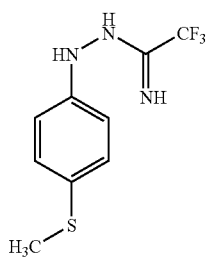

Formula 8

1.0 g (5.24 mmol) of 4-methylsulfanylphenylhydrazine hydrochloride was dissolved in 40 ml of a 1:1 mixed solvent of methanol and tetrahydrofuran and 0.80 ml (5.76 mmol) of triethylamine was added dropwise. The reaction mixture was stirred at room temperature for 30 minutes and 0.90 g (6.81 mmol) of 85% trifluoro acetimidine was added dropwise. The reaction mixture was stirred at room temperature for 24 hours. When the reaction was completed, water and ethyl acetate were added to the reaction mixture. The water layer was twice extracted with ethyl acetate. The combined organic layer was once washed with saturated sodium chloride solution, dried over anhydrous magnesium sulfate, and filtered under reduced pressure. The obtained crude product was purified by flash column chromatography (ethyl acetate/n-hexane=2/8) to give 0.88 g of the title compound as a liquid (yield 67%).

¹H-NMR (400 MHz, CDCl₃): δ 2.55 (s, 3H), 5.45 (s, 2H, br), 7.40 (d, 2H, J=8.0 Hz), 7.60 (d, 2H, J=8.0 Hz), 9.70 (s,1 H).

EXAMPLE 2

N-(5-methanesulfonylpyridin-2-yl)trifluoroacetamidrazone

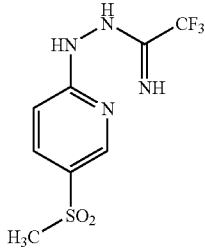

Formula 9

205 mg (yield 54%) of the title compound as a solid was prepared in the same manner as in Example 1 except using 300 mg (1.34 mmol) of 5-methanesulfonylpyridin-2-yl hydrazine hydrochloride instead of 4-methylsulfanylphenylhydrazine hydrochloride.

¹H-NMR (400 MHz, CDCl₃): δ 2.90 (s, 3H), 5.65 (s, 2H, br), 6.95 (dd, 1H, J₁=9.0 Hz, J₂=2.8 Hz), 7.80 (dd, 1H, J₁=9.0 Hz, J₂=2.0 Hz), 9.70 (d, 1H, J=2.8 Hz), 9.75 (s,1H).

EXAMPLE 3

N-(2-methanesulfonylpyridin-5-yl)trifluoroacetamidrazone

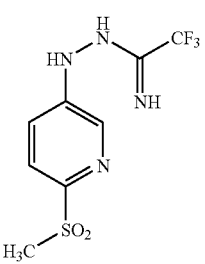

Formula 10

194 mg (yield 51%) of the title compound as a solid was prepared in the same manner as in Example 1 except using 300 mg (1.34 mmol) of 2-methanesulfonylpyridin-5-yl hydrazine hydrochloride instead of 4-methylsulfanylphenylhydrazine hydrochloride.

¹H-NMR (400 MHz, CDCl₃): δ 3.35 (s, 3H), 5.65 (s, 2H, br), 6.95 (dd, 1 H, J₁=9.0 Hz, J₂=2.8 Hz), 7.80 (dd, 1 H, J₁=9.0 Hz, J₂=2.0 Hz), 9.70 (d, 1 H, J=2.8 Hz), 9.75 (s, 1 H).

EXAMPLE 4

N-(6-methanesulfonylpyridazin-3-yl)trifluoroacetamidrazone

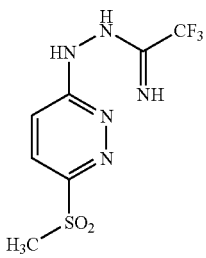

Formula 11

0.8 g (yield 64%) of the title compound as a solid was prepared in the same manner as in Example 1 except using 1.0 g (4.45 mmol) of 6-methanesulfonylpyridazin-3-yl hydrazine hydrochloride instead of 4-methylsulfanylphenylhydrazine hydrochloride.

¹H-NMR (400 MHz, CDCl₃): δ 3.45 (s, 3H), 7.15 (s, 2H, br), 7.45 (d, 1H, J=9.5 Hz), 8.00 (d, 1H, J=9.5 Hz), 10.80 (s, 1H).

EXAMPLE 5

N-(4-sulfonamidophenyl)trifluoroacetamidrazone

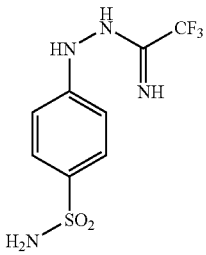

Formula 12

0.9 g (yield 68%) of the title compound as a solid was prepared in the same manner as in Example 1 except using 1.0 g (4.47 mmol) of 4-hydrazinobenzenesulfonamide hydrochloride instead of 4-methylsulfanylphenylhydrazine hydrochloride.

¹H-NMR (400 MHz, CDCl₃): δ 5.45 (s, 2H, br), 7.31 (s, 2H), 7.40 (d, 2H, J=8.0 Hz), 7.60 (d, 2H, J=8.0 Hz), 9.70 (s, 1H).

EXAMPLE 6

1-(4-methylsulfanylphenyl)-5-p-tolyl-3-trifluoromethyl-1H-[1,2,4]triazole

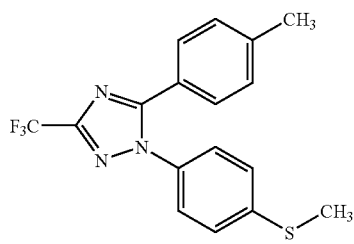

Formula 13

220 mg (0.88 mmol) of N-(4-methylsulfanylphenyl)trifluoroacetamidrazone was dissolved in 5 ml of 1,4-dioxane and 0.08 ml (0.97 mmol) of pyridine was added dropwise. The reaction mixture was stirred at room temperature for 10 minutes and 150 mg (0.97 mmol) of p-toluoyl chloride was added dropwise. The reaction mixture was stirred at the boiling point under reflux for 24 hours. When the reaction was completed, the reaction mixture was cooled to room temperature and water and ethyl acetate were added thereto. The water layer was twice extracted with ethyl acetate. The combined organic layer was once washed with saturated sodium chloride solution and dried over anhydrous magnesium sulfate, and filtered under reduced pressure. The obtained crude product was purified by flash column chromatography (ethyl acetate/n-hexane=2:8) to give 210 mg of the title compound as an oil (yield 65%).

$^1$H-NMR (400 MHz, CDCl$_3$): δ 2.35 (s, 3H), 2.55 (s, 3H), 7.15 (d, 2H, J=8.0 Hz), 7.20–7.30 (m, 4H), 7.45 (d, 2H, J=8.0 Hz).

EXAMPLE 7

1-(4-methylsulfanylphenyl)-5-phenyl-3-trifluoromethyl-1H-[1,2,4]triazole

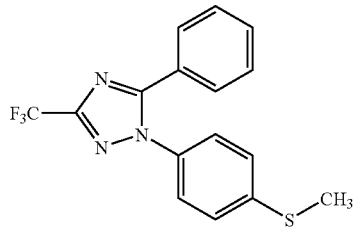

Formula 14

210 mg (yield 71%) of the title compound as an oil was prepared in the same manner as in Example 6 except using 140 mg (0.97 mmol) of benzoyl chloride instead of p-toluoyl chloride. The title compound was used in the next step without further purification.

EXAMPLE 8

5-(4-chlorophenyl)-1-(4-methylsulfanylphenyl)-3-trifluoromethyl-1H-[1,2,4]triazole

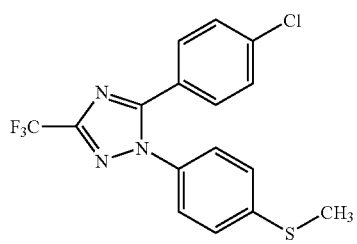

Formula 15

210 mg (yield 65%) of the title compound as an oil was prepared in the same manner as in Example 6 except using 170 mg (0.97 mmol) of 4-chlorobenzoyl chloride instead of p-toluoyl chloride. The title compound was used in the next step without further purification or identification.

EXAMPLE 9

5-(4-bromophenyl)-1-(4-methylsulfanylphenyl)-3-trifluoromethyl-1H-[1,2,4]triazole

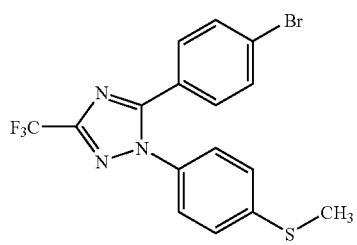

Formula 16

280 mg (yield 76%) of the title compound as an oil was prepared in the same manner as in Example 6 except using 213 mg (0.97 mmol) of 4-bromobenzoyl chloride instead of p-toluoyl chloride. The title compound was used in the next step without further purification or identification.

EXAMPLE 10

1-(4-methylsulfanylphenyl)-5-(4-methoxyphenyl)-3-trifluoromethyl-1H-[1,2,4]triazole

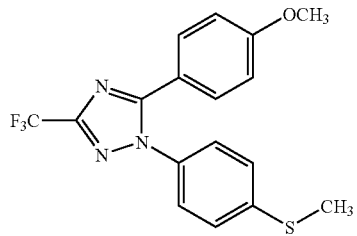

Formula 17

203 mg (yield 69%) of the title compound as an oil was prepared in the same manner as in Example 6 except using 165 mg (0.97 mmol) of p-anisoyl chloride instead of p-toluoyl chloride. The title compound was used in the next step without further purification or identification.

EXAMPLE 11

5-(3-bromophenyl)-1-(4-methylsulfanylphenyl)-3-trifluoromethyl-1H-[1,2,4]triazole

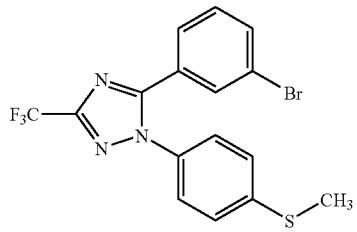

Formula 18

280 mg (yield 76%) of the title compound as an oil was prepared in the same manner as in Example 6 except using 213 mg (0.97 mmol) of 3-bromobenzoyl chloride instead of p-toluoyl chloride. The title compound was used in the next step without further purification or identification.

EXAMPLE 12

5-(3-chlorophenyl)-1-(4-methylsulfanylphenyl)-3-trifluoromethyl-1H-[1,2,4]triazole

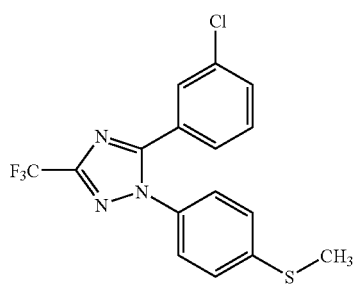

Formula 19

182 mg (yield 72%) of the title compound as an oil was prepared in the same manner as in Example 6 except using 170 mg (0.97 mmol) of 3-chlorobenzoyl chloride instead of p-toluoyl chloride. The title compound was used in the next step without further purification or identification.

EXAMPLE 13

5-(3-trifluoromethylphenyl)-1-(4-methylsulfanylphenyl)-3-trifluoromethyl-1H-[1,2,4]triazole

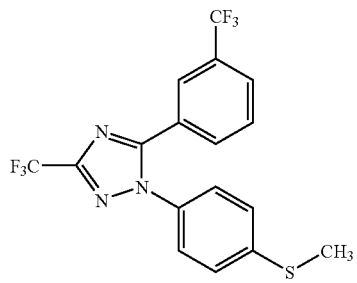

Formula 20

209 mg (yield 64%) of the title compound as an oil was prepared in the same manner as in Example 6 except using 202 mg (0.97 mmol) of 3-trifluorometyl benzoyl chloride instead of p-toluoyl chloride. The title compound was used in the next step without further purification or identification.

EXAMPLE 14

5-(2,4-dimethoxyphenyl)-1-(4-methylsulfanylphenyl)-3-trifluoromethyl-1H-[1,2,4]triazole

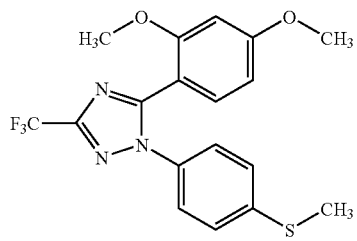

Formula 21

188 mg (yield 54%) of the title compound as an oil was prepared in the same manner as in Example 6 except using 195 mg (0.97 mmol) of 2,4-dimethoxybenzoyl chloride instead of p-toluoyl chloride. The title compound was used in the next step without further purification or identification.

EXAMPLE 15

5-styryl-1-(4-methylsulfanylphenyl)-3-trifluoromethyl-1H-[1,2,4]triazole

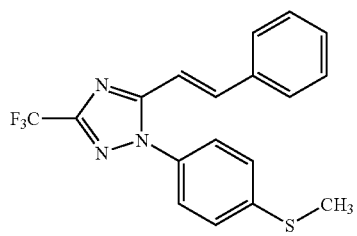

Formula 22

232 mg (yield 73%) of the title compound as an oil was prepared in the same manner as in Example 6 except using 161 mg (0.97 mmol) of cynamoyl chloride instead of p-toluoyl chloride. The title compound was used in the next step without further purification or identification.

EXAMPLE 16

5-[2-(4-methoxyphenyl)vinyl]-1-(4-methylsulfanylphenyl)-3-trifluoromethyl-1H-[1,2,4]triazole

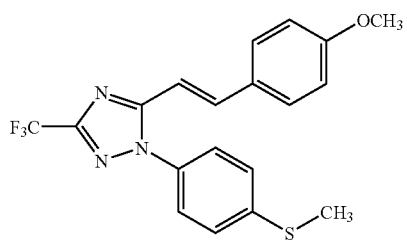

Formula 23

189 mg (yield 55%) of the title compound as an oil was prepared in the same manner as in Example 6 except using 191 mg (0.97 mmol) of 4-methoxycynamoyl chloride instead of p-toluoyl chloride. The title compound was used in the next step without further purification or identification.

EXAMPLE 17

5-(4-ethoxyphenyl)-1-(4-methylsulfanylphenyl)-3-trifluoromethyl-1H-[1,2,4]triazole

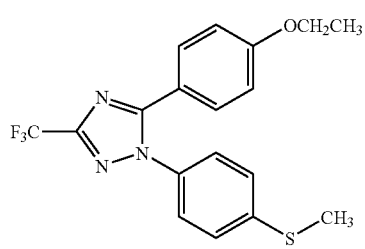

Formula 24

243 mg (yield 73%) of the title compound as an oil was prepared in the same manner as in Example 6 except using 181 mg (0.97 mmol) of 4-ethoxybenzoyl chloride instead of p-toluoyl chloride. The title compound was used in the next step without further purification or identification.

EXAMPLE 18

5-(4-t-butylphenyl)-1-(4-methylsulfanylphenyl)-3-trifluoromethyl-1H-[1,2,4]triazole

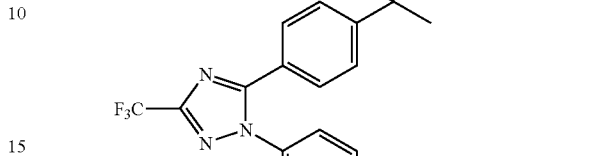

Formula 25

282 mg (yield 82%) of the title compound as an oil was prepared in the same manner as in Example 6 except using 193 mg (0.97 mmol) of 4-t-butylbenzoyl chloride instead of p-toluoyl chloride. The title compound was used in the next step without further purification or identification.

EXAMPLE 19

5-(4-cyanophenyl)-1-(4-methylsulfanylphenyl)-3-trifluoromethyl-1H-[1,2,4]triazole

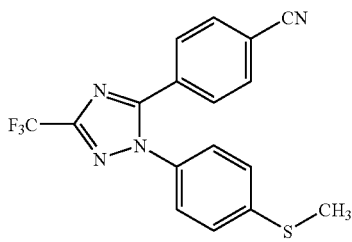

Formula 26

165 mg (yield 52%) of the title compound as an oil was prepared in the same manner as in Example 6 except using 163 mg (0.97 mmol) of 4-cyanobenzoyl chloride instead of p-toluoyl chloride. The title compound was used in the next step without further purification or identification.

EXAMPLE 20

5-(4-nitro-2-chlorophenyl)-1-(4-methylsulfanylphenyl)-3-trifluoromethyl-1H-[1,2,4]triazole

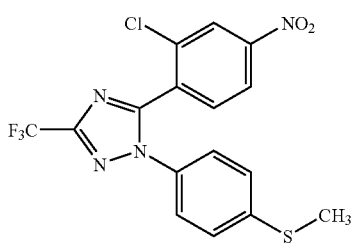

Formula 27

248 mg (yield 68%) of the title compound as an oil was prepared in the same manner as in Example 6 except using 213 mg (0.97 mmol) of 4-nitro-2-chlorobenzoyl chloride instead of p-toluoyl chloride. The title compound was used in the next step without further purification or identification.

EXAMPLE 21

5-(3-chloro-4-methoxyphenyl)-1-(4-methylsulfanylphenyl)-3-trifluoromethyl-1H-[1,2,4]triazole

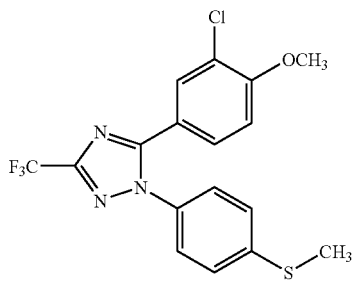

Formula 28

215 mg (yield 61%) of the title compound as an oil was prepared in the same manner as in Example 6 except using 200 mg (0.97 mmol) of 3-chloro-4-methoxybenzoyl chloride instead of p-toluoyl chloride. The title compound was used in the next step without further purification or identification.

EXAMPLE 22

5-benzo[1,3]dioxol-5-yl-1-(4-methylsulfanylphenyl)-3-trifluoromethyl-1H-[1,2,4]triazole

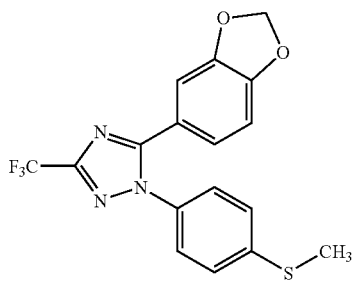

Formula 29

206 mg (yield 59%) of the title compound as an oil was prepared in the same manner as in Example 6 except using 180 mg (0.97 mmol) of benzo[1,3]dioxol-5-yl carbonyl chloride instead of p-toluoyl chloride. The title compound was used in the next step without further purification or identification.

EXAMPLE 23

4-[2-(4-methylsulfanylphenyl)-5-trifluoromethyl-2H-[1,2,4]triazol-3-yl]pyridine

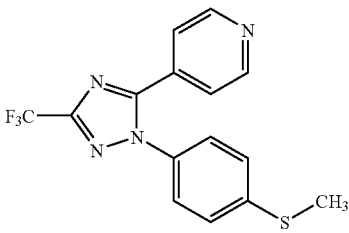

Formula 30

121 mg (yield 41%) of the title compound as an oil was prepared in the same manner as in Example 6 except using 138 mg (0.97 mmol) of isonicotinyl chloride instead of p-toluoyl chloride. The title compound was used in the next step without further purification or identification.

EXAMPLE 24

1-(4-methanesulfonylphenyl)-5-p-tolyl-3-trifluoromethyl-1H-[1,2,4]triazole

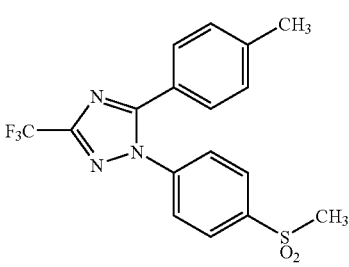

Formula 31

310 mg (0.89 mmol) of 1-(4-methylsulfanylphenyl)-5-p-tolyl-3-trifluoro-1H-[1,2,4]triazole was dissolved in a mixed solvent of dichloromethane (10 ml) and methanol (2 ml) and 710 mg (1.16 mmol) of 80% MMPP was slowly added dropwise. The reaction mixture was stirred at room temperature for 8 hours. When the reaction was completed, the reaction mixture was filtered. The filtrate was washed with sodium bicarbonate and saturated sodium chloride solution (1× each), dried over anhydrous magnesium sulfate, filtered, and concentrated under reduced pressure. The obtained crude product was purified by flash column chromatography (ethyl acetate/n-hexane=7:3) to give 308 mg (yield 91%) of the title compound as a solid.

¹H-NMR (400 MHz, CDCl₃): δ 2.45 (s, 3H), 3.15 (s, 3H), 7.23 (d, 2H, J=8.2 Hz), 7.38 (d, 2H, J=8.2 Hz), 7.63 (d, 2H, J=8.7 Hz), 8.03 (d, 2H, J=8.7 Hz). m.p.: 176–178° C.

EXAMPLE 25

1-(4-methanesulfonylphenyl)-5-phenyl-3-trifluoromethyl-1H-[1,2,4]triazole

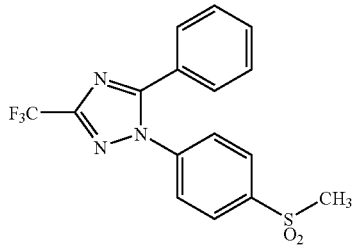

Formula 32

283 mg (yield 86%) of the title compound as a solid was prepared in the same manner as in Example 24 except using 300 mg (0.89 mmol) of 1-(4-methylsulfanylphenyl)-5-phenyl-3-trifluoro-1H-[1,2,4]triazole instead of 1-(4-methylsulfanylphenyl)-5-p-tolyl-3-trifluoro-1H-[1,2,4]triazole.

¹H-NMR (400 MHz, CDCl₃): δ 3.15 (s, 3H), 7.42–7.48 (m, 2H), 7.50–7.55 (m, 3H), 7.63 (d, 2H, J=8.6 Hz), 8.03 (d, 2H, J=8.6 Hz). m.p.: 153–154° C.

EXAMPLE 26

5-(4-chlorophenyl)-1-(4-methanesulfonylphenyl)-3-trifluoromethyl-1H-[1,2,4]triazole

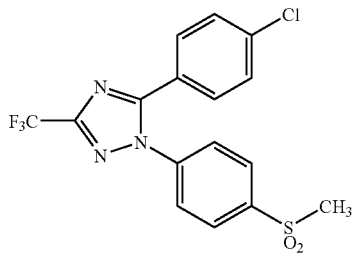

Formula 33

294 mg (yield 82%) of the title compound as a solid was prepared in the same manner as in Example 24 except using 330 mg (0.89 mmol) of 5-(4-chlorophenyl)-1-(4-methylsulfanylphenyl)-3-trifluoro-1H-[1,2,4]triazole instead of 1-(4-methylsulfanylphenyl)-5-p-tolyl-3-trifluoro-1H-[1,2,4]triazole.

¹H-NMR (400 MHz, CDCl₃): δ 3.15 (s, 3H), 7.40–7.50 (m, 4H), 7.60 (d, 2H, J=6.7 Hz), 8.03 (d, 2H, J=6.7 Hz). m.p.: 190–192° C.

EXAMPLE 27

5-(4-bromophenyl)-1-(4-methanesulfonylphenyl)-3-trifluoromethyl-1H-[1,2,4]triazole

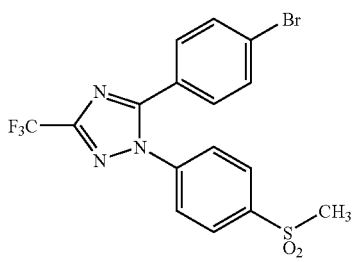

Formula 34

365 mg (yield 92%) of the title compound as a solid was prepared in the same manner as in Example 24 except using 370 mg (0.89 mmol) of 5-(4-bromophenyl)-1-(4-methylsulfanylphenyl)-3-trifluoro-1H-[1,2,4]triazole instead of 1-(4-methylsulfanylphenyl)-5-p-tolyl-3-trifluoro-1H-[1,2,4]triazole.

¹H-NMR (400 MHz, CDCl₃): δ 3.15 (s, 3H), 7.35 (d, 2H, J=8.5 Hz), 7.50–7.60 (m, 4H), 8.03 (d, 2H, J=6.3 Hz). m.p.: 198–199° C.

EXAMPLE 28

1-(4-methanesulfonylphenyl)-5-(4-methoxyphenyl)-3-trifluoromethyl-1H-[1,2,4]triazole

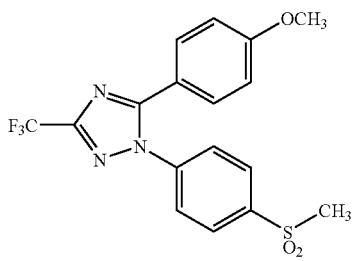

Formula 35

300 mg (yield 85%) of the title compound as a solid was prepared in the same manner as in Example 24 except using 325 mg (0.89 mmol) of 1-(4-methylsulfanylphenyl)-5-(4-methoxyphenyl)-3-trifluoro-1H-[1,2,4]triazole instead of 1-(4-methylsulfanylphenyl)-5-p-tolyl-3-trifluoro-1H-[1,2,4]triazole.

¹H-NMR (400 MHz, CDCl₃): δ 3.15 (s, 3H), 3.90 (s, 3H), 6.90 (d, 2H, J=6.9 Hz), 7.35 (d; 2H, J=6.9 Hz), 7.65 (d, 2H, J=8.7 Hz), 8.03 (d, 2H, J=8.7 Hz). m.p.: 155–156° C.

EXAMPLE 29

5-(3-bromophenyl)-1-(4-methanesulfonylphenyl)-3-trifluoromethyl-1H-[1,2,4]triazole

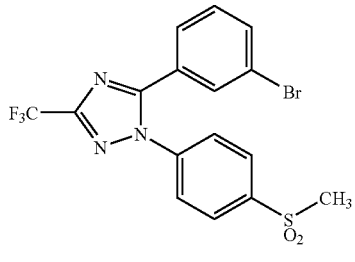

Formula 36

365 mg (yield 92%) of the title compound as a solid was prepared in the same manner as in Example 24 except using 370 mg (0.89 mmol) of 5-(3-bromophenyl)-1-(4-methylsulfanylphenyl)-3-trifluoro-1H-[1,2,4]triazole instead of 1-(4-methylsulfanylphenyl)-5-p-tolyl-3-trifluoro-1H-[1,2,4]triazole.

$^1$H-NMR (400 MHz, CDCl$_3$): δ 3.15 (s, 3H), 7.35–7.72 (m, 6H), 7.92 (d, 2H, J=8.7 Hz). m.p.: 195–196° C.

EXAMPLE 30

5-(3-chlorophenyl)-1-(4-methanesulfonylphenyl)-3-trifluoromethyl-1H-[1,2,4]triazole

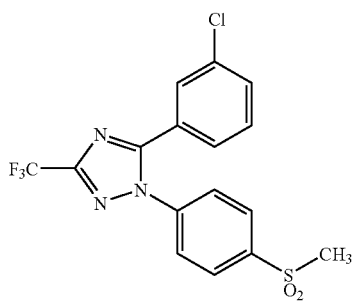

Formula 37

326 mg (yield 91%) of the title compound as a solid was prepared in the same manner as in Example 24 except using 330 mg (0.89 mmol) of 5-(3-chlorophenyl)-1-(4-methylsulfanylphenyl)-3-trifluoro-1H-[1,2,4]triazole instead of 1-(4-methylsulfanylphenyl)-5-p-tolyl-3-trifluoro-1H-[1,2,4]triazole.

$^1$H-NMR (400 MHz, CDCl$_3$): δ 3.11 (s, 3H), 7.00 (d, 1H, J=9.0 Hz), 7.28 (m, 1 H), 7.35 (d, 1H, J=9.0 Hz), 7.62 (s, 1H), 7.64 (d, 2H, J=9.2 Hz), 8.09 (d, 2H, J=9.2 Hz). m.p.: 188–190° C.

EXAMPLE 31

5-(3-trifluoromethylphenyl)-1-(4-methanesulfonylphenyl)-3-trifluoromethyl-1H-[1,2,4]triazole

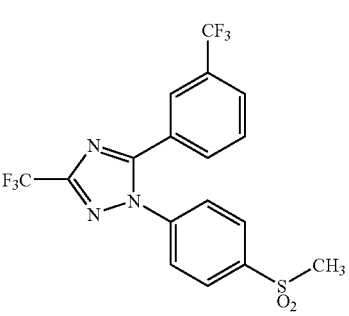

Formula 38

340 mg (yield 88%) of the title compound as a solid was prepared in the same manner as in Example 24 except using 360 mg (0.89 mmol) of 5-(3-trifluoromethylphenyl)-1-(4-methylsulfanylphenyl)-3-trifluoro-1H-[1,2,4]triazole instead of 1-(4-methylsulfanylphenyl)-5-p-tolyl-3-trifluoro-1H-[1,2,4]triazole.

$^1$H-NMR (400 MHz, CDCl$_3$): δ 3.10 (s, 3H), 7.56 (m, 1H), 7.61–7.64 (m, 3H), 7.79 (d, 1 H, J=4.0 Hz), 7.86 (s, 1H), 8.09 (d, 2H, J=8.8 Hz). m.p.: 135–137° C.

EXAMPLE 32

5-(2,4-dimethoxyphenyl)-1-(4-methanesulfonylphenyl)-3-trifluoromethyl-1H-[1,2,4]triazole

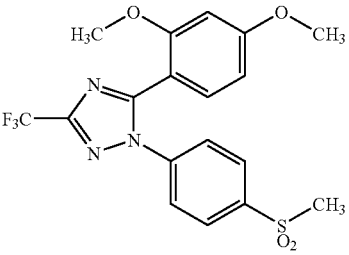

Formula 39

357 mg (yield 94%) of the title compound as a solid was prepared in the same manner as in Example 24 except using 350 mg (0.89 mmol) of 5-(2,4-dimethoxyphenyl)-1-(4-methylsulfanylphenyl)-3-trifluoro-1H-[1,2,4]triazole instead of 1-(4-methylsulfanylphenyl)-5-p-tolyl-3-trifluoro-1H-[1,2,4]triazole.

$^1$H-NMR (400 MHz, CDCl$_3$): δ 3.11 (s, 3H), 3.26 (s, 3H), 3.84 (s, 3H), 6.34 (d, 1H, J=2.4 Hz), 6.66 (dd, 1H, J=8.4 Hz, J=2.4 Hz), 7.58 (d, 1H, J=8.4 Hz), 7.69 (d, 2H, J=8.8 Hz), 7.98 (d, 2H, J=8.8 Hz). m.p.: 110–112° C.

EXAMPLE 33

5-styryl-1-(4-methanesulfonylphenyl)-3-trifluoromethyl-1H-[1,2,4]triazole

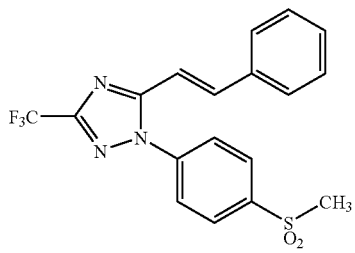

Formula 40

287 mg (yield 82%) of the title compound as a solid was prepared in the same manner as in Example 24 except using 320 mg (0.89 mmol) of 5-styryl-1-(4-methylsulfanylphenyl)-3-trifluoro-1H-[1,2,4]triazole instead of 1-(4-methylsulfanylphenyl)-5-p-tolyl-3-trifluoro-1H-[1,2,4]triazole.

$^1$H-NMR (400 MHz, CDCl$_3$): δ 3.15 (s, 3H), 6.83 (d, 1H, J=15.9 Hz), 7.39–7.41 (m, 3H), 7.52–7.54 (m, 2H), 7.82 (d, 2H, J=8.6 Hz), 8.01 (d, 1H, J=15.9 Hz), 8.21 (d, 2H, J=8.6 Hz). m.p.: 168–170° C.

EXAMPLE 34

5-[2-(4-methoxyphenyl)vinyl]-1-(4-methanesulfonylphenyl)-3-trifluoromethyl-1H-[1,2,4]triazole

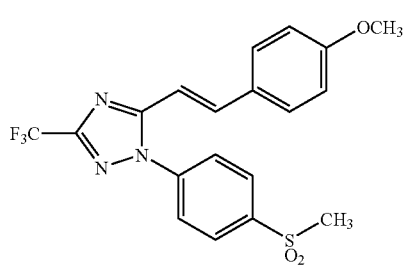

Formula 41

340 mg (yield 91%) of the title compound as a solid was prepared in the same manner as in Example 24 except using 378 mg (0.89 mmol) of 5-[2-(4-methoxyphenyl)vinyl]-1-(4-methylsulfanylphenyl )-3-trifluoromethyl-1H-[1,2,4]triazole instead of 1-(4-methylsulfanylphenyl)-5-p-tolyl-3-trifluoro-1H-[1,2,4]triazole.

$^1$H-NMR (400 MHz, CDCl$_3$): δ 3.17 (s, 3H), 3.85 (s, 3H), 6.75 (d, 1H, J=15.9 Hz), 6.96 (d, 2H, J=8.7 Hz), 7.50 (d, 2H, J=8.7 Hz), 7.82 (d, 2H, J=8.6 Hz), 7.95 (d, 1H, J=15.9 Hz), 8.21 (d, 2H, J=8.6 Hz).

EXAMPLE 35

5-(4-ethoxyphenyl)-1-(4-methanesulfonylphenyl)-3-trifluoromethyl-1H-[1,2,4]triazole

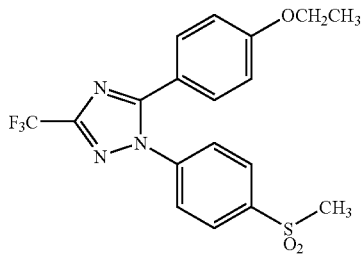

Formula 42

300 mg (yield 82%) of the title compound as a solid was prepared in the same manner as in Example 24 except using 337 mg (0.89 mmol) of 5-(4-ethoxyphenyl)-1-(4-methylsulfanylphenyl)-3-trifluoromethyl-1H-[1,2,4]triazole instead of 1-(4-methylsulfanylphenyl)-5-p-tolyl-3-trifluoro-1H-[1,2,4]triazole.

$^1$H-NMR (400 MHz, CDCl$_3$): δ 1.45 (t, 3H, J=7.0 Hz), 3.15 (s, 3H), 4.10 (q, 2H, J=7.0 Hz), 6.91 (d, 2H, J=8.9 Hz), 7.45 (d, 2H, J=8.9 Hz), 7.65 (d, 2H, J=8.7 Hz), 8.05 (d, 2H, J=8.7 Hz). m.p.: 152–154° C.

EXAMPLE 36

5-(4-t-butylphenyl)-1-(4-methanesulfonylphenyl)-3-trifluoromethyl-1H-[1,2,4]triazole

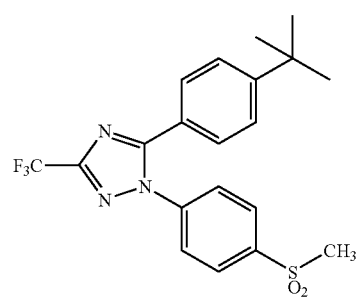

Formula 43

343 mg (yield 91%) of the title compound as a solid was prepared in the same manner as in Example 24 except using 348 mg (0.89 mmol) of 5-(4-t-butylphenyl)-1-(4-methylsulfanylphenyl)-3-trifluoromethyl-1H-[1,2,4]triazole instead of 1-(4-methylsulfanylphenyl)-5-p-tolyl-3-trifluoro-1H-[1,2,4]triazole.

$^1$H-NMR (400 MHz, CDCl$_3$): δ 1.30 (s, 9H), 3.15 (s, 3H), 7.40–7.50 (m, 4H), 7.68 (d, 2H, J=9.0 Hz), 8.08 (d, 2H, J=9.0 Hz). m.p.: 81–82° C.

EXAMPLE 37

5-(4-cyanophenyl)-1-(4-methanesulfonylphenyl)-3-trifluoromethyl-1H-[1,2,4]triazole

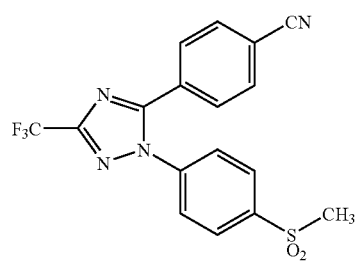

Formula 44

320 mg (yield 92%) of the title compound as a solid was prepared in the same manner as in Example 24 except using 320 mg (0.89 mmol) of 5-(4-cyanophenyl)-1-(4-methylsulfanylphenyl)-3-trifluoromethyl- 1H-[1,2,4]triazole instead of 1-(4-methylsulfanylphenyl)-5-p-tolyl-3-trifluoro-1H-[1,2,4]triazole.

$^1$H-NMR (400 MHz, CDCl$_3$): δ 3.15 (s, 3H), 7.64 (d, 2H, J=8.8 Hz), 7.68 (d, 2H, J=8.8 Hz), 7.75 (d, 2H, J=8.7 Hz), 8.13 (d, 2H, J=8.7 Hz). m.p.: 109–111° C.

EXAMPLE 38

5-(4-nitro-2-chlorophenyl)-1-(4-methanesulfonylphenyl)-3-trifluoromethyl-1H-[1,2,4]triazole

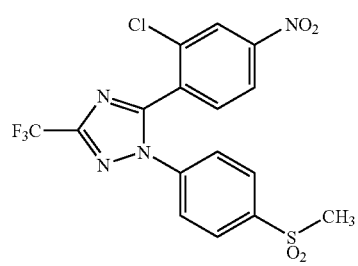

Formula 45

314 mg (yield 79%) of the title compound as a solid was prepared in the same manner as in Example 24 except using 369 mg (0.89 mmol) of 5-(4-nitro-2-chlorophenyl)-1-(4-methylsulfanylphenyl)-3-trifluoromethyl-1H-[1,2,4]triazole instead of 1-(4-methylsulfanylphenyl)-5-p-tolyl-3-trifluoro-1H-[1,2,4]triazole.

$^1$H-NMR (400 MHz, CDCl$_3$): δ 3.15 (s, 3H), 7.51 (d, 2H, J=8.6 Hz), 7.83 (d, 1H, J=9.0 Hz), 7.97 (d, 2H, J=8.6 Hz), 8.29 (d, 1H, J=9.0 Hz), 8.32 (s, 1H). m.p.: 110–111° C.

EXAMPLE 39

5-(3-chloro-4-methoxyphenyl)-1-(4-methanesulfonylphenyl)-3-trifluoromethyl-1H-[1,2,4]triazole

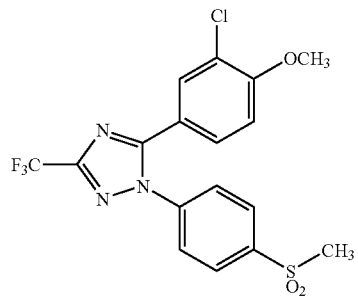

Formula 46

319 mg (yield 83%) of the title compound as a solid was prepared in the same manner as in Example 24 except using 356 mg (0.89 mmol) of 5-(3-chloro-4-methoxyphenyl)-1-(4-methylsulfanylphenyl)-3-trifluoromethyl-1H-[1,2,4]triazole instead of 1-(4-methylsulfanylphenyl)-5-p-tolyl-3-trifluoro-1H-[1,2,4]triazole.

$^1$H-NMR (400 MHz, CDCl$_3$): δ 3.15 (s, 3H), 3.95 (s, 3H), 6.90 (d, 1H, J=8.6 Hz), 7.25 (dd, 1 H, J$_1$=8.6 Hz, J$_2$=2.5 Hz), 7.75 (dd, 2H, J$_1$=6.8 Hz, J$_2$=2.0 Hz), 7.76 (d, 1H, J=2.5 Hz), 8.08 (dd, 2H, J$_1$=8.6 Hz, J$_2$=2.0 Hz).

EXAMPLE 40

5-benzo[1,3]dioxol-5-yl-1-(4-methanesulfonylphenyl)-3-trifluoromethyl-1H-[1,2,4]triazole

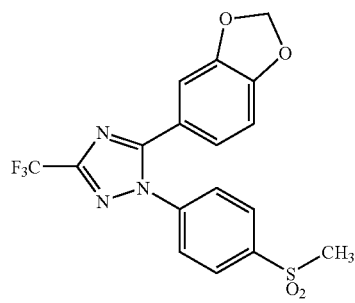

Formula 47

322 mg (yield 88%) of the title compound as a solid was prepared in the same manner as in Example 24 except using 337 mg (0.89 mmol) of 5-benzo[1,3]dioxol-5-yl-1-(4-methylsulfanylphenyl)-3-trifluoromethyl-1H-[1,2,4]triazole instead of 1-(4-methylsulfanylphenyl)-5-p-tolyl-3-trifluoro-1H-[1,2,4]triazole.

$^1$H-NMR (400 MHz, CDCl$_3$): δ 3.15 (s, 3H), 6.05 (s, 2H), 6.82 (d, 1H, J=7.5 Hz), 6.97–7.02 (m, 2H), 7.65 (d, 2H, J=8.6 Hz), 8.05 (d, 2H, J=8.6 Hz).

EXAMPLE 41

4-[2-(4-methanesulfonylphenyl)-5-trifluoromethyl-2H-[1,2,4]triazol-3-yl]pyridine

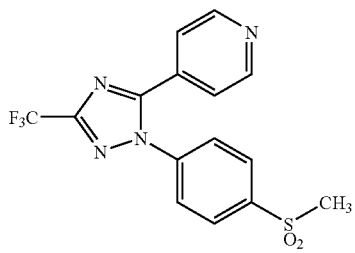

Formula 48

244 mg (yield 72%) of the title compound as a solid was prepared in the same manner as in Example 24 except using 299 mg (0.89 mmol) of 4-[2-(4-methylsulfanylphenyl)-5-trifluoromethyl-2H-[1,2,4]triazol-3-yl]pyridine instead of 1-(4-methylsulfanylphenyl)-5-p-tolyl-3-trifluoro-1H-[1,2,4]triazole.

$^1$H-NMR (400 MHz, CDCl$_3$): δ 3.15 (s, 3H), 7.45 (d, 2H, J=6.0 Hz), 7.65 (d, 2H, J=8.0 Hz), 8.10 (d, 2H, J=8.0 Hz), 8.75 (d, 2H, J=6.0 Hz). m.p.: 180–182° C.

EXAMPLE 42

4-(5-p-tolyl-3-trifluoromethyl-[1,2,4]triazol-1-yl)benzenesulfonamide

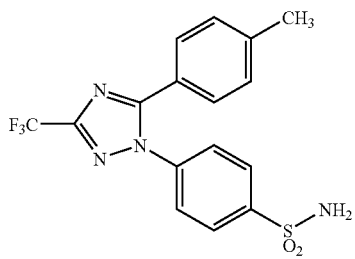

Formula 49

120 mg (0.32 mmol) of 1-(4-methanesulfonylphenyl)-5-p-tolyl-3-trifluoro-1H-[1,2,4]triazole was dissolved in 2 ml of anhydrous tetrahydrofuran and the reaction temperature was adjusted to 0° C. 0.18 ml (0.54 mmol) of 3 M solution of methyl magnesium chloride in tetrahydrofuran was added dropwise and the reaction temperature was raised to room temperature. The reaction mixture was stirred at that temperature for 3 hours. 0.9 ml (0.90 mmol) of 1 M solution of tributylborane in tetrahydrofuran was added dropwise and refluxed for 18 hours. The reaction temperature was cooled to 0° C. Then, a solution in which 150 mg (1.34 mmol) of hydroxylamine-O-sulfonic acid and 2.56 mg (3.20 mmol) of sodium acetic acid were dissolved in 2 ml of water was slowly added and the reaction mixture was stirred at room temperature for 3 hours. When the reaction was completed, water and ethyl acetate were added, and stirred. Then, the resultant solution was three times extracted with ethyl acetate. The combined organic layer was once washed with saturated sodium chloride solution, dried over anhydrous magnesium sulfate, filtered under reduced pressure, and concentrated under reduced pressure. The obtained crude product was purified by flash column chromatography (ethyl acetate/n-hexane=7/3) to give 63 mg (yield 52%) of the title compound as a solid.

$^1$H-NMR (400 MHz, DMSO-d$_6$): δ 2.45 (s, 3H), 7.20 (d, 2H, J=8.2 Hz), 7.35 (d, 2H, J=8.2 Hz), 7.52 (s, 2H), 7.70 (d, 2H, J=6.6 Hz), 7.98 (d, 2H, J=6.6 Hz). m.p.: 245–247° C.

EXAMPLE 43

4-[5-(4-methoxyphenyl)-3-trifluoromethyl-[1,2,4]triazol-1-yl]benzene sulfonamide

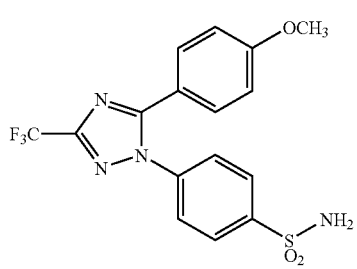

Formula 50

68 mg (yield 53%) of the title compound as a solid was prepared in the same manner as in Example 42 except using 127 mg (0.32 mmol) of 1-(4-methylsulfanylphenyl)-5-(4-methoxyphenyl)-3-trifluoro-1H-[1,2,4]triazole instead of 1-(4-methanesulfonylphenyl)-5-p-tolyl-3-trifluoro-1H-[1,2,4]triazole.

$^1$H-NMR (400 MHz, DMSO-d$_6$): δ 3.85(s, 3H), 6.96 (d, 2H, J=6.9 Hz), 7.45 (d, 2H, J=6.9 Hz), 7.55 (s, 2H), 7.75 (d, 2H, J=8.6 Hz), 7.95 (d, 2H, J=8.6 Hz). m.p.: 251–253° C.

EXAMPLE 44

4-[5-(4-bromophenyl)-3-trifluoromethyl-[1,2,4]triazol-1-yl]benzene sulfonamide

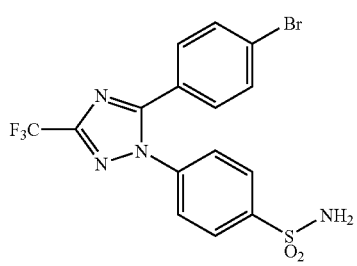

Formula 51

250 mg (0.88 mmol) of N-(4-sulfonamidophenyl)trifluoroacetamidrazone was dissolved in 5 ml of 1,4-dioxane and 0.08 ml (0.97 mmol) of pyridine was added dropwise. The reaction mixture was stirred at room temperature for 10 minutes and 212 mg (0.97 mmol) of 4-bromobenzoyl chloride was added dropwise. The reaction mixture was refluxed for 24 hours. When the reaction was completed, the reaction mixture was cooled to room temperature and water and ethyl acetate were added thereto. The water layer was twice extracted with ethyl acetate. The combined organic layer was once washed with saturated sodium chloride solution, dried over anhydrous magnesium sulfate, and filtered under reduced pressure. The obtained crude product was purified by flash column chromatography (ethyl acetate/n-hexane=1/1) to give 208 mg (yield 53%) of the title compound as an oil.

$^1$H-NMR (400 MHz, CDCl$_3$): δ 4.95 (br, s, 2H), 7.39 (d, 2H, J=8.7 Hz), 7.58–7.62 (m, 4H), 8.05 (d, 2H, J=8.7 Hz).

EXAMPLE 45

2-[5-(4-bromophenyl)-3-trifluoromethyl-[1,2,4]triazol-1-yl]-5-methanesulfonyl pyridine

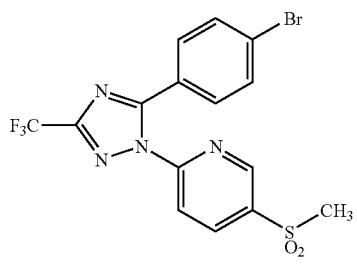

Formula 52

130 mg (0.46 mmol) of N-(5-methanesulfonylpyridin-2-yl)trifluoroacetamidrazone was dissolved in 5 ml of 1,4-dioxane and 0.04 ml (0.51 mmol) of pyridine was added dropwise. The reaction mixture was stirred at room temperature for 10 minutes and 115 mg (0.51 mmol) of 4-bromobenzoyl chloride was added dropwise. The reaction mixture was stirred at 110° C. under reflux for 24 hours. When the reaction was completed, the reaction mixture was cooled to room temperature and water and ethyl acetate were added thereto. The water layer was twice extracted with ethyl acetate. The combined organic layer was once washed with saturated sodium chloride solution, dried over anhydrous magnesium sulfate, and filtered under reduced pressure. The obtained crude product was purified by flash column chromatography (ethyl acetate/n-hexane=3:7) to give 107 mg (yield 52%) of the title compound as a solid.

$^1$H-NMR (400 MHz, CDCl$_3$): δ 3.42 (s, 3H), 7.55 (d, 2H, J=6.7 Hz), 7.70 (d, 2H, J=6.7 Hz), 8.15 (d, 1H, J=8.5 Hz), 8.65 (dd, 1H, J$_1$=8.5 Hz, J$_2$=2.1 Hz), 8.95 (d, 1H, J=2.1 Hz). m.p.: 143–145° C.

EXAMPLE 46

2-[5-(4-methoxyphenyl)-3-trifluoromethyl-[1.2.4]triazol-1-yl]-5-methanesulfonyl pyridine

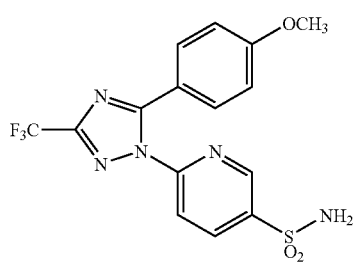

Formula 53

108 mg (yield 59%) of the title compound as a solid was prepared in the same manner as in Example 45 except using 87 mg (0.51 mmol) of p-anisoyl chloride instead of 4-bromobenzoyl chloride.

$^1$H-NMR (400 MHz, CDCl$_3$): δ 3.25(s, 3H), 3.85 (s, 3H), 6.90 (d, 2H, J=6.8 Hz), 7.50 (d, 2H, J=6.7 Hz), 7.95 (d, 1H, J=8.5 Hz), 8.45 (dd, 1H, J$_1$=8.5 Hz, J$_2$=2.1 Hz), 8.95 (d, 1H, J=2.1 Hz). m.p.: 138–139° C.

EXAMPLE 47

2-methanesulfonyl-5-[5-(4-bromophenyl)-3-trifluoromethyl-[1,2,4]triazol-1-yl]pyridine

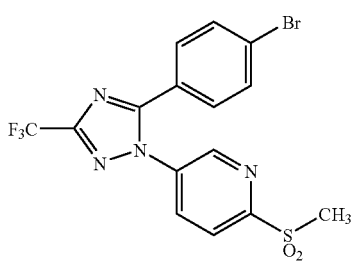

Formula 54

130 mg (0.46 mmol) of N-(2-methanesulfonylpyridin-5-yl)trifluoroacetamidrazone was dissolved in 5 ml of 1,4-dioxane and 0.04 ml (0.51 mmol) of pyridine was added dropwise. The reaction mixture was stirred at room temperature for 10 minutes and 115 mg (0.51 mmol) of 4-bromobenzoyl chloride was added dropwise. The reaction mixture was stirred at 110° C. under reflux for 24 hours. When the reaction was completed, the reaction mixture was cooled to room temperature and water and ethyl acetate were added thereto. The water layer was twice extracted with ethyl acetate. The combined organic layer was once washed with saturated sodium chloride solution, dried over anhydrous magnesium sulfate, and filtered under reduced pressure. The obtained crude. product was purified by flash column chromatography (ethyl acetate/n-hexane=3:7) to give 107 mg (yield 52%) of the title compound as a solid.

$^1$H-NMR (400 MHz, CDCl$_3$): δ 3.42 (s, 3H), 7.55 (d, 2H, J=6.7 Hz), 7.70 (d, 2H, J=6.7 Hz), 8.22 (d, 1H, J=8.5 Hz), 8.55 (dd, 1H, J$_1$=8.5 Hz, J$_2$=2.1 Hz), 8.95 (d, 1H, J=2.1 Hz). m.p.: 141–143° C.

EXAMPLE 48

2-methanesulfonyl-5-[5-(4-methoxyphenyl)-3-trifluoromethyl-[1,2,4]triazol-1-yl]pyridine

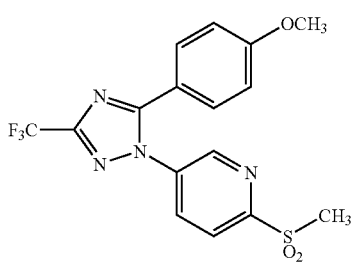

Formula 55

108 mg (yield 59%) of the title compound as a solid was prepared in the same manner as in Example 47 except using 87 mg (0.51 mmol) of p-anisoyl chloride instead of 4-bromobenzoyl chloride.

$^1$H-NMR (400 MHz, CDCl$_3$): δ 3.25(s, 3H), 3.85 (s, 3H), 6.90 (d, 2H, J=6.8 Hz), 7.50 (d, 2H, J=6.7 Hz), 7.85 (d, 1H, J=8.5 Hz), 8.35 (dd, 1H, J$_1$=8.5 Hz, J$_2$=2.1 Hz), 8.90 (d, 1H, J=2.1 Hz). m.p. 136–137° C.

EXAMPLE 49

3-[5-(4-bromophenyl)-3-trifluoromethyl-[1,2,4]triazol-1-yl]-6-methanesulfonyl pyridazine

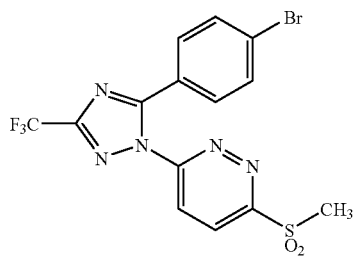

Formula 56

310 mg (1.09 mmol) of N-(6-methanesulfonylpyridazin-3-yl)trifluoroacetamidrazone was dissolved in 10 ml of 1,4-dioxane and 0.10 ml (1.20 mmol) of pyridine was added dropwise. The reaction mixture was stirred at room temperature for 10 minutes and 264 mg (1.20 mmol) of 4-bromobenzoyl chloride was added dropwise. The reaction mixture was stirred at 110° C. under reflux for 24 hours. When the reaction was completed, the reaction mixture was cooled to room temperature and water and ethyl acetate were added thereto. The water layer was twice extracted with ethyl acetate. The combined organic layer was once washed with saturated sodium chloride solution, dried over anhydrous magnesium sulfate, and filtered under reduced pressure. The obtained crude product was purified by flash column chromatography (ethyl acetate/n-hexane=3:7) to give 220 mg (yield 45%) of the title compound as a solid.

$^1$H-NMR (400 MHz, CDCl$_3$): δ 3.42 (s, 3H), 7.55 (d, 2H, J=8.5 Hz), 7.62 (d, 2H, J=8.5 Hz), 8.38 (d, 1 H, J=9.0 Hz), 8.45 (d, 1 H, J=9.0 Hz). m.p.: 174–181° C.

EXAMPLE 50

3-[5-(4-methoxyphenyl)-3-trifluoromethyl-[1.2.4]triazol-1-yl]-6-methanesulfonyl pyridazine

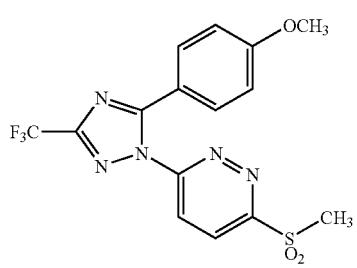

Formula 57

183 mg (yield 42%) of the title compound as a solid was prepared in the same manner as in Example 49 except using 205 mg (0.51 mmol) of p-anisoyl chloride instead of 4-bromobenzoyl chloride.

$^1$H-NMR (400 MHz, CDCl$_3$): δ 3.42(s, 3H), 3.85 (s, 3H), 6.85 (d, 2H, J=6.8 Hz), 7.55 (d, 2H, J=6.8 Hz), 8.20 (d, 1H, J=9.1 Hz), 8.35 (d, 1H, J=9.1 Hz). m.p.: 185–186° C.

Experiments

1. Evaluation of Selective COX-2 Inhibitory Activity

1) Method

In order to pharmacologically determine the selective COX-2 inhibitory activity, the percentages of the COX-1 and COX-2 inhibition of the compounds of the present invention illustrated in the Examples were measured by the following methods.

a. Assay for the COX-1 Inhibitory Activity Using U-937

U-937 human lymphoma cells (Korean Cell Line Bank, Seoul, Korea, Accession Number: 21593) were cultured and centrifuged. The collected cells were diluted with HBSS (×1, Hank's balanced salt solution) to a concentration of 1×10$^6$ cells/ml. 1 ml of the dilute cell solution was placed into each well of 12-well plates. 5 μl of 1 μM solution of a test compound in DMSO and 5 μl of DMSO as a control were added to the wells. The wells were incubated in CO$_2$ incubator at 37° C. for 15 minutes. Separately, 10 mM stock solution of arachidonic acid in ethanol was diluted ten times in ethanol to prepare 1 mM solution of arachidonic acid. Arachidonic acid acts as a substrate. 10 μl of the 1 mM solution of arachidonic acid was added to each well and incubated at CO$_2$ incubator at 37° C. for 30 minutes. The cell solution of each well was placed in a centrifuge test tube and centrifuged at 10,000 rpm at 4° C. for 5 minutes. The concentration of PGE2 in the collected cells and the supernatant was quantified by means of a monoclonal kit (Cayman Chemicals). The percentages of PGE2 inhibition in a group of the test compound-treated cells in relation to a group of the DMSO-treated cells were calculated. Based on the calculated values, the COX-1 inhibitory activities were evaluated.

b. Assay for the COX-2 Inhibitory Activity Using RAW 264.7 Cell Line

2×10$^6$ cells of RAW 264.7 cell line (Korean Cell Line Bank, Seoul, Korea, Accession Number: 40071) were inoculated into each well of 12-well plates. Each well was treated with 250 μM of aspirin and incubated at 37° C. for 2 hours. After the culture media were replaced with new culture media, the new culture media were treated with a test compound (10nM) and incubated for 30 minutes. Then, each well was treated with interferon γ (100 units/ml) and lipopolysaccharide (LPS, 100 ng/ml) and incubated for 18 hours. The culture media were transferred to another test tubes. The concentration of PGE2 was quantified by means of the EIA kit (Cayman Chemicals).

2) Test Results

The test results are presented in Table 1 below. The percentages of the COX inhibition were calculated according to the following equation:

% Inhibition=(concentration of PGE2 in test compound-untreated sample–concentration of PGE2 in test compound-treated sample)/(concentration of PGE2 in test compound-untreated sample)×100

TABLE 1

Cyclooxygenase (COX) Inhibition (%)

| Samples | COX-1 (1 μM) | COX-2 (10 nM) |
| --- | --- | --- |
| Reference (Valdecoxib) | 28.8 | 5.47 |
| Example 25 | 29.2 | 7.62 |
| Example 26 | 38.8 | 10.53 |
| Example 27 | 13.8 | 16.04 |
| Example 28 | 10.1 | 28.62 |
| Example 29 | 16.7 | 6.23 |
| Example 30 | 18.6 | 7.32 |
| Example 31 | 16.5 | 5.66 |
| Example 32 | 19.9 | 12.6 |
| Example 33 | 19.2 | 19.23 |
| Example 34 | 23.5 | 26.82 |
| Example 35 | 11.8 | 38.65 |
| Example 36 | 21.6 | 6.23 |
| Example 37 | 23.7 | 8.92 |
| Example 38 | 19.5 | 5.95 |
| Example 39 | 12.5 | 32.62 |
| Example 40 | 18.7 | 33.73 |
| Example 41 | 16.7 | 8.88 |
| Example 42 | 38.0 | 12.08 |
| Example 43 | 34.6 | 32.32 |
| Example 44 | 23.1 | 29.86 |
| Example 45 | 14.6 | 33.63 |
| Example 46 | 12.6 | 42.32 |
| Example 47 | 21.9 | 4.26 |
| Example 48 | 28.8 | 5.63 |
| Example 49 | 14.6 | 3.21 |
| Example 50 | 10.6 | 4.32 |

3) Evaluation

The in vitro test results about the percentages of the COX-1 and COX-2 inhibition are listed in Table 1.

As shown in Table 1, inhibition (%) ratios of COX-2 to COX-1 in Examples 24 and 50 were equal to or higher than that in the reference, Valdecoxib. This indicates that selective inhibition of COX-2 to COX-1 of the present compound is the same as or superior to that of the reference. In particular, in the case of 1-(4-methanesulfonylphenyl)-5-(4-methoxyphenyl)-3-trifluoro-1H-[1,2,4]triazole of Example 28, 1-(4-methanesulfonylphenyl)-5-(4-ethoxyphenyl)-3-trifluoro-1H-[1,2,4]triazole of Example 35, 5-(3-chloro-4-methoxyphenyl)-1-(4-methanesulfonylphenyl)-3-trifluoromethyl-1H-[1,2,4]triazole of Example 39, 5-bezo[1,3]dioxol-5-yl-1-(4-methanesulfonylphenyl)-3-trifluoromethyl-1H-[1,2,4]triazole of Example 40, 4-[5-(4-bromophenyl)-3-trifluoromethyl-[1,2,4]triazol-1-yl]benzenesulfonamide of Example 44, 2-[5-(4-bromophenyl)-3-trifluoromethyl-[1,2,4]triazol-1-yl]-5-methanesulfonyl pyridine of Example 45, and 2-[5-(4-methoxyphenyl)-3-trifluoromethyl-[1,2,4]triazol-1-yl]-5-methanesulfonyl pyridine of Example 46, the COX-2 inhibitory activities were remarkably enhanced in comparison with the reference. At the same time, the COX-1 inhibitory activities were the same as or lower than that of the reference. Therefore, it can be said that these compounds have excellent selectivities.

All the compounds of Examples except Examples 47, 49, and 50 exhibited the COX-2 inhibitory activities higher than the reference. Based on this result, it can be seen that the present compounds have reduced side effects due to enhanced selectivity and improved relief effects of fever, pain, and inflammation, compared to the reference.

2. Carrageenan-induced Paw Edema Test in Rats

1) Method

The day before the test date, rats were selected in each group so that the average body weight was as close as possible, and the rats were fasted by feed withdrawal prior to the test. At the test date, the rats were orally administered with the test compounds and a control material. After 1 hour, the volume ($V_{0h}$) of a predetermined portion of the left hind foot of the rats was measured with a plethysmometer. 100 μl of 1% carrageenan solution was subcutaneously injected to the left hind foot of the rats using a syringe with 1 ml capacity. Three hours after the injection of the carrageenan, the volume ($V_{3h}$) of the predetermined portion of the foot was again measured. The foot swelling variation ($T_{3h}-T_{0h}$) in a group of test compound-treated rats was compared with that of a group of control material-treated rats. With the supposition of 0% inhibition by the control (control material-treated rats), the inhibition percentage of edema of each test compound was determined.

2) Test Results

The test results are presented in Table 2 below.

TABLE 2

Cyclooxygenase (COX) inhibitory effect (% inhibition)

| Samples | Inhibitory effect (% inhibition) |
| --- | --- |
| Reference 1 (Indomethacine) | 40.1 |
| Reference 2 (Celecoxib) | 23.9 |
| Example 27 | 21.7 |
| Example 28 | 23.3 |
| Example 34 | 19.3 |
| Example 35 | 32.3 |
| Example 43 | 39.1 |
| Example 44 | 28.8 |
| Example 45 | 21.6 |
| Example 46 | 33.4 |

3) Evaluation

The in vivo test results of the percentage of COX inhibition are listed in Table 2.

As shown in Table 2, the % inhibition of the compounds in Examples 27 to 46 against COX was almost the same as or much higher than that of the Celecoxib. This indicates that the compounds of the present invention have almost the same or higher COX inhibitory effects, compared to the Celecoxib. In particular, in the case of 1-(4-methanesulfonylphenyl)-5-(4-ethoxyphenyl)-3-trifluoro- 1H-[1,2,4]triazole of Example 35, 4-[5-(4-methoxyphenyl )-3-trifluoromethyl-[1,2,4]triazol-1-yl]benzenesulfonamide of Example 43, 4-[5-(4-bromophenyl)-3-trifluoromethyl-[1,2,4]triazol-1-yl]benzenesulfonamide of Example 44, and 2-[5-(4-methoxyphenyl)-3-trifluoromethyl-[1,2,4]triazol-1-yl]-5-methanesulfonyl pyridine of Example 46, the COX inhibitory effects were remarkably improved in comparison with the Celecoxib.

In addition, all the compounds of Examples except Example 34 exhibited the same or higher COX inhibitory effects in comparison with the Celecoxib. Therefore, it can be seen that the compounds of the present invention have improved relief effects of fever, pain, and inflammation.

As apparent from the above description, the present invention provides a 1,2,4-triazole derivative or a non-toxic salt thereof, a preparation method thereof, and a pharmaceutical composition containing the derivative or the salt as an active ingredient. The pharmaceutical composition is effective in reducing fever, pain, and inflammation. In particular, as a result of reduction of the side effects of conventional nonsteroidal antiinflammatory agents, the pharmaceutical composition is useful for treating patients with peptic ulcer disease, gastritis, regional enteritis, ulcerative colitis, diverticullitis, gastrorrhagia, or hypoprothrombinemia.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A 1,2,4-triazole derivative represented by formula 1:

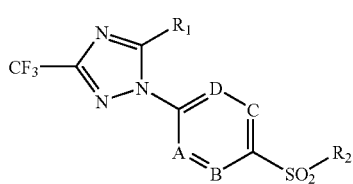

Formula 1 wherein:
R$_1$ is a C$_3$–C$_6$ cycloalkyl group; a C$_3$–C$_6$ cycloalkenyl group; a phenyl group; a phenyl group substituted with one or more selected from the group consisting of a C$_1$–C$_6$ alkyl group, a C$_1$–C$_6$ haloalkyl group, a C$_1$–C$_6$ alkoxy group, a C$_1$–C$_6$ haloalkoxy group, a halogen group, an amino group, a monoalkylamino group, a dialkylamino group, a nitro group, and a cyano group; a styrenyl group; a C$_1$–C$_6$ alkoxy styrenyl group; or a pyridyl group;
R$_2$ is a methyl group; and
A, B, C, or D is independently carbon;
or a non-toxic salt thereof.

2. The 1,2,4-triazole derivative according to claim 1, which is selected from the group consisting of:
1-(4-methanesulfonylphenyl)-5-phenyl-3-trifluoromethyl-1H-[1,2,4]triazole;
5-(4-bromophenyl)-1-(4-methanesulfonylphenyl)-3-trifluoromethyl-1H-[1,2,4]triazole;
5-(3-bromophenyl)-1-(4-methanesulfonylphenyl)-3-trifluoromethyl-1H-[1,2,4]triazole;
5-(4-fluorophenyl )-1-(4-methanesulfonylphenyl)-3-trifluoromethyl-1H-[1,2,4]triazole;
5-(3,5-dichloro-4-methoxyphenyl)-1-(4-methanesulfonylphenyl)-3-trifluoromethyl-1H-[1,2,4]triazole;
5-(4-chlorophenyl)-1-(4-methanesulfonylphenyl)-3-trifluoromethyl-1H-[1,2,4]triazole;
5-(3,4-dichlorophenyl)-1-(4-methanesulfonylphenyl)-3-trifluoromethyl-1H-[1,2,4]triazole;
5-(3,4-dimethoxyphenyl)-1-(4-methanesulfonylphenyl)-3-trifluoromethyl-1H-[1,2,4]triazole;
5-(3,4-difluorophenyl)-1-(4-methanesulfonylphenyl)-3-trifluoromethyl-1H-[1,2,4]triazole;
1-(4-methanesulfonylphenyl)-5-(4-methoxyphenyl)-3-trifluoromethyl-1H-[1,2,4]triazole;
5-(3,4-dimethoxyphenyl)-1-(4-methanesulfonylphenyl)-3-trifluoromethyl-1H-[1,2,4]triazole;
1-(4-methanesulfonylphenyl)-5-p-tolyl-3-trifluoromethyl-1H-[1,2,4]triazole;
5-(3,4-dimethylphenyl)-1-(4-methanesulfonylphenyl)-3-trifluoromethyl-1H-[1,2,4]triazole;
5-(3-chloro-4-methylphenyl)-1-(4-methanesulfonylphenyl)-3-trifluoromethyl-1H-[1,2,4]triazole;
5-(4-chloro-3-methylphenyl)-1-(4-methanesulfonylphenyl)-3-trifluoromethyl-1H-[1,2,4]triazole;
5-(3-chloro-4-methoxyphenyl)-1-(4-methanesulfonylphenyl)-3-trifluoromethyl-1H-[1,2,4]triazole;
5-(4-chloro-3-methoxyphenyl)-1-(4-methanesulfonylphenyl)-3-trifluoromethyl-1H-[1,2,4]triazole;
5-(3-fluoro-4-methylphenyl)-1-(4-methanesulfonylphenyl)-3-trifluoromethyl-1H-[1,2,4]triazole;
5-(4-fluoro-3-methylphenyl)-1-(4-methanesulfonylphenyl)-3-trifluoromethyl-1H-[1,2,4]triazole;
5-(3-fluoro-4-methoxyphenyl)-1-(4-methanesulfonylphenyl)-3-trifluoromethyl-1H-[1,2,4]triazole;
1-(4-methanesulfonylphenyl)-3-trifluoromethyl-5-(4-trifluoromethylphenyl)-1H-[1,2,4]triazole;
5-(4-ethoxyphenyl)-1-(4-methanesulfonylphenyl)-3-trifluoromethyl-1H-[1,2,4]triazole;
1-(4-methanesulfonylphenyl)-5-(4-trifluoromethoxyphenyl)-3-trifluoromethyl-1H-[1,2,4]triazole;
5-(4-t-butylphenyl)-1-(4-methanesulfonylphenyl)-3-trifluoromethyl-1H-[1,2,4]triazole;
5-(4-cyanophenyl)-1-(4-methanesulfonylphenyl)-3-trifluoromethyl-1H-[1,2,4]triazole;
5-[4-(N-methylamino)phenyl]-1-(4-methanesulfonylphenyl)-3-trifluoromethyl-1H-[1,2,4]triazole;
5-[4-(N,N-dimethylamino)phenyl]-1-(4-methanesulfonylphenyl)-3-trifluoromethyl-1H-[1,2,4]triazole;
5-(4-aminophenyl)-1-(4-methanesulfonylphenyl)-3-trifluoromethyl-1H-[1,2,4]triazole;
5-(3-trifluoromethylphenyl)-1-(4-methanesulfonylphenyl)-3-trifluoromethyl-1H-[1,2,4]triazole;
5-(3-methoxyphenyl)-1-(4-methanesulfonylphenyl)-3-trifluoromethyl-1H-[1,2,4]triazole;
1-(4-methanesulfonylphenyl)-5-m-tolyl-3-trifluoromethyl-1H-[1,2,4]triazole;
1-(4-methanesulfonylphenyl)-5-o-tolyl-3-trifluoromethyl-1H-[1,2,4]triazole;
5-(2-bromophenyl)-1-(4-methanesulfonylphenyl)-3-trifluoromethyl-1H-[1,2,4]triazole;
5-(2-methoxyphenyl)-1-(4-methanesulfonylphenyl)-3-trifluoromethyl-1H-[1,2,4]triazole;
5-(2,4-difluorophenyl)-1-(4-methanesulfonylphenyl)-3-trifluoromethyl-1H-[1,2,4]triazole;
5-(2,5-difluorophenyl)-1-(4-methanesulfonylphenyl)-3-trifluoromethyl-1H-[1,2,4]triazole;
5-(2,4,5-trifluorophenyl)-1-(4-methanesulfonylphenyl)-3-trifluoromethyl-1H-[1,2,4]triazole;
5-(2,3-dichlorophenyl)-1-(4-methanesulfonylphenyl)-3-trifluoromethyl-1H-[1,2,4]triazole;
5-(2,4-dichlorophenyl)-1-(4-methanesulfonylphenyl)-3-trifluoromethyl-1H-[1,2,4]triazole;
5-(3,5-difluorophenyl)-1-(4-methanesulfonylphenyl)-3-trifluoromethyl-1H-[1,2,4]triazole;
5-(3,5-dimethoxyphenyl)-1-(4-methanesulfonylphenyl)-3-trifluoromethyl-1H-[1,2,4]triazole;
5-(2,4-dimethoxyphenyl)-1-(4-methanesulfonylphenyl)-3-trifluoromethyl-1H-[1,2,4]triazole;
5-(3,4,5-trimethoxyphenyl)-1-(4-methanesulfonylphenyl)-3-trifluoromethyl-1H-[1,2,4]triazole;
5-(2-fluoro-4-trifluoromethylphenyl)-1-(4-methanesulfonylphenyl)-3-trifluoromethyl-1H-[1,2,4]triazole;
5-(2-chloro-4-nitrophenyl)-1-(4-methanesulfonylphenyl)-3-trifluoromethyl-1H-[1,2,4]triazole;
5-(2,4-dichloro-5-fluorophenyl)-1-(4-methanesulfonylphenyl)-3-trifluoromethyl-1H-[1,2,4]triazole;
5-(3-fluoro-4-methylphenyl)-1-(4-methanesulfonylphenyl)-3-trifluoromethyl-1H-[1,2,4]triazole;
5-benzo[1,3]dioxol-5-yl-1-(4-methanesulfonylphenyl)-3-trifluoromethyl-1H-[1,2,4]triazole;

3-[2-(4-methanesulfonylphenyl)-5-trifluoromethyl-2H-[1,2,4]triazol-3-yl]pyridine;

4-[2-(4-methanesulfonylphenyl)-5-trifluoromethyl-2H-[1,2,4]triazol-3-yl]pyridine;

5-cyclohexyl-1-(4-methanesulfonylphenyl)-3-trifluoromethyl-1H-[1,2,4]triazole;

5-cyclohexen-1-yl-1-(4-methanesulfonylphenyl)-3-trifluoromethyl-1H-[1,2,4]triazole;

5-styryl-1-(4-methanesulfonylphenyl)-3-trifluoromethyl-1H-[1,2,4]triazole; and

5-[2-(4-methoxyphenyl)-vinyl]-1-(4-methanesulfonylphenyl)-3-trifluoromethyl-1H-[1,2,4]triazole;

or a non toxic salt thereof.

\* \* \* \* \*